US006764226B1

(12) United States Patent
Freeman et al.

(10) Patent No.: US 6,764,226 B1
(45) Date of Patent: Jul. 20, 2004

(54) DEVICE FOR TEMPERATURE CONTROLLED HOUSING OF A PLANAR OPTICAL COMPONENT

(75) Inventors: Neville John Freeman, Utikinton (GB); Graham Cross, Little Stainton (GB)

(73) Assignee: Fairfield Sensors Limited, Manchester (GB)

( * ) Notice: Subject to any disclaimer, the term of this patent is extended or adjusted under 35 U.S.C. 154(b) by 160 days.

(21) Appl. No.: 10/088,292

(22) PCT Filed: Sep. 22, 2000

(86) PCT No.: PCT/GB00/03635

§ 371 (c)(1), (2), (4) Date: Mar. 15, 2002

(87) PCT Pub. No.: WO01/22068

PCT Pub. Date: Mar. 29, 2001

(30) Foreign Application Priority Data

Sep. 24, 1999 (GB) .......................................... 9922601

(51) Int. Cl.[7] .............................................. G02B 6/36

(52) U.S. Cl. ...................................................... 385/88

(58) Field of Search .............................. 385/88, 90–94; 374/20

(56) References Cited

U.S. PATENT DOCUMENTS

| | | | | | |
|---|---|---|---|---|---|
| 4,083,224 | A | * | 4/1978 | Gayst | 374/19 |
| 4,804,274 | A | * | 2/1989 | Green | 374/17 |
| 5,007,733 | A | * | 4/1991 | Laurent et al. | 356/70 |
| 5,022,045 | A | * | 6/1991 | Elliott | 374/20 |
| 5,641,230 | A | * | 6/1997 | Okubo | 374/20 |
| 5,692,085 | A | * | 11/1997 | Jongerius et al. | 385/91 |
| 6,076,959 | A | * | 6/2000 | Nagasawa | 374/20 |

* cited by examiner

*Primary Examiner*—J. F. Duverne
(74) *Attorney, Agent, or Firm*—Howrey Simon Arnold & White, L.L.P.

(57) ABSTRACT

The present invention relates to an improved device for housing a planar optical component for use in chemical sensing for example which permits fine temperature control and disposal of heat.

37 Claims, 17 Drawing Sheets

15Ce 15Cd 15Ca 15Cf 15Ca 15Cd 15Ca 15Cc 15Cb

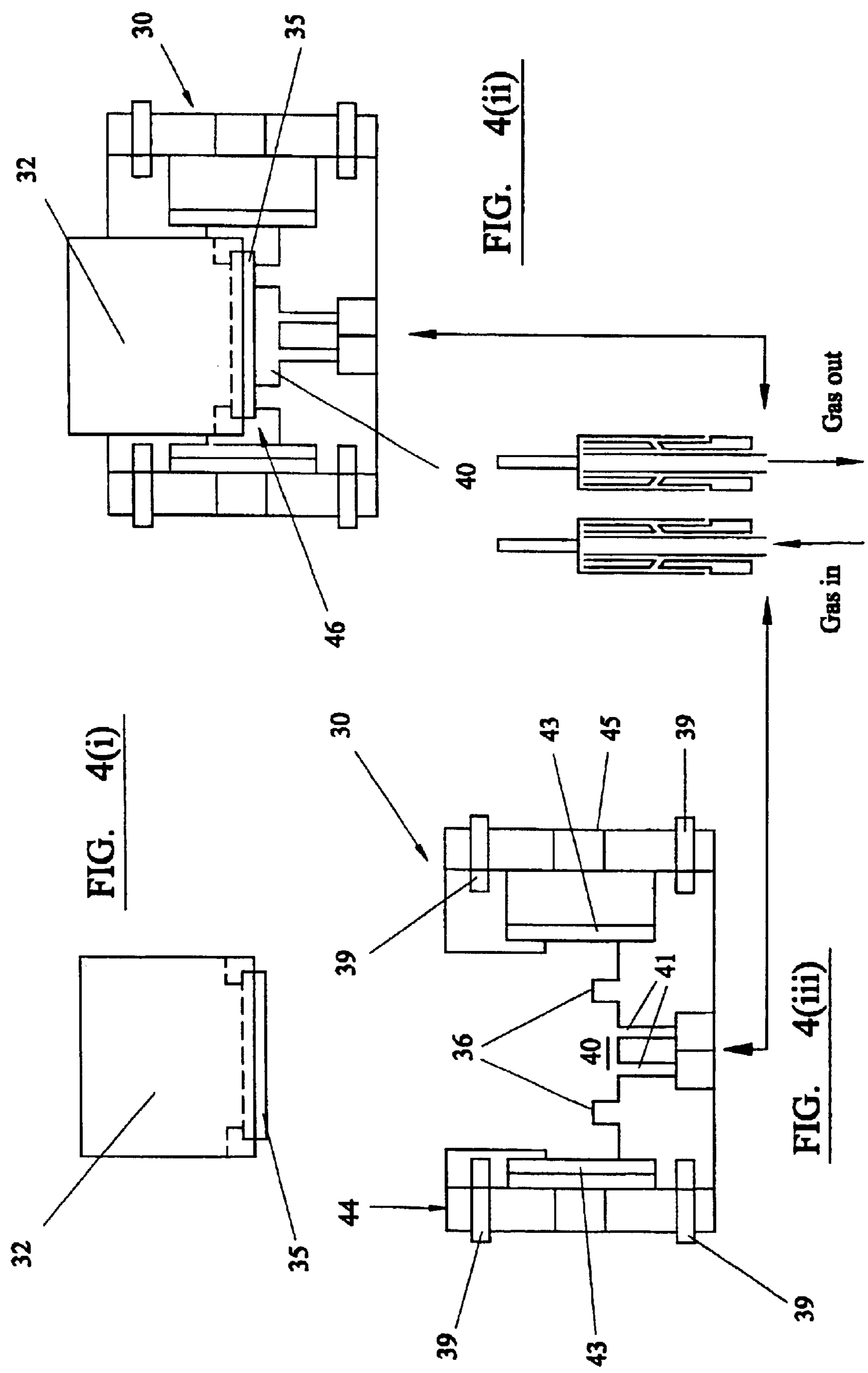
FIG. 4(i)
FIG. 4(ii)
FIG. 4(iii)

14Aa
14Ab
14Ac
14Ad
14Ae
14Ba
14Bb
14Bc
14Bd
14Be
14Bf
14Bg
14Bh
14Bi
14Bj
14Bk
14Bl
14Bm
14Ca
14Cb
14Cc

15Aa
15Aa
15Ac
15Ad
15Ab

15Ba
15Bb
15Bd
15Bc
15Ba
15Ba
15Bc
15Be
15Bb

15Ca
15Cb
15Cc
15Cd
15Ca
15Ca
15Cd
15Cf
15Ce

DEVICE FOR TEMPERATURE CONTROLLED HOUSING OF A PLANAR OPTICAL COMPONENT

Priority is claimed under 35 USC §371 of International Application Number PCT/GB00/03536, filed Sep. 22, 2000 which claims priority under Article 4 of the Paris Convention to United Kingdom Patent Application Number 9922601.1, filed 24 Sep. 1999.

The present invention relates to an improved device for housing a planar optical component for use in chemical sensing for example.

New chemical sensor technologies using optical techniques (in particular interferometric techniques) are providing new high performance devices. Whilst these devices are relatively simple in terms of components, the tolerances required in the assembly-procedure can be extremely onerous. Of these, end illuminated interferometric devices are perhaps the most demanding. In such cases, sub-micron misalignment between the electromagnetic radiation source (typically a collimated, focussed laser) and the sensor substrate itself may be sufficient to prevent its correct operation.

There are several situations which may lead to distorted output from a conventional device. Thus, the light beam may pass over the top of the planar optical component and distort the output received by-the detector. Similarly, where the device comprises a planar sensing waveguide and a planar reference waveguide, if the light misses a waveguide or fails to illuminate both equally, the output may be lost or distorted. Thus, if any of the components (eg light source, lenses, polarisers, sensors etc) are misaligned by as little as $2\times10^{-7}$ metres (200 nm) the performance of the device will be adversely effected. The provision of a device which ensures that waveguides are illuminated equally without admitting stray light represents a significant technical challenge.

More generally, there is a need for sensor assemblies of simpler construction and improved reliability. The range and applicability of chemical sensors could be greatly enhanced if it were possible to achieve lower manufacturing costs and greater robustness. An important consideration in developing suitable devices is temperature management. This imposes various design constraints related to the thermal mass of areas requiring insulation and the disposal of unwanted heat into the environment.

The present invention seeks to provide an improved device for housing a planar optical component such as a chemical sensor which is-capable of ultra high precision temperature control. The device is advantageously robust and gives enhanced signal to noise ratios (sensitivity). Moreover, the invention seeks to provide an optical (interferometric) chemical sensor device which is simple to machine and assemble and fault tolerant in terms of construction errors and which may be used to obtain reliable information relating to the changes occurring within the device.

Thus viewed from one aspect the present invention provides a device comprising:

an optical assembly adapted to mount a planar optical component (eg a sensor) so as to define a longitudinal path through the device in which the planar optical component is effectively exposed in free space and including guiding means for correlating along said longitudinal path the position of said planar optical component and of a source of electromagnetic radiation, whereby to expose said planar optical component to said electromagnetic radiation along said longitudinal path whilst substantially eliminating stray electromagnetic radiation, wherein the optical assembly comprises a cavity which permits access to a face of the planar optical component or a face of a base with which the planar optical component is in intimate thermal contact whereby to enable an inner temperature controller to be positioned in thermal contact with the planar optical component for controlling the temperature of the planar optical component.

The inner temperature controller is capable of permitting fine temperature control of the planar optical component (eg sensor) and may be a heat pump or thermo-electric controller capable of providing or removing heat as desired. In a preferred embodiment, the inner temperature controller is an inner Peltier assembly capable of adding heat to or dissipating heat from the planar optical component. The inner Peltier assembly may comprise an inner Peltier mounted on an inner Peltier mount. The inner Peltier mount conveniently provides thermal mass. Preferably, the Peltier mount has a concave underside to optimise thermal contact with the planar optical component (or its base). The inner Peltier and inner Peltier mount may be provided with suitable insulation as desired.

Preferably the planar optical component is a sensor. In a preferred embodiment, the sensor is mounted on a sensor base and is in intimate thermal contact therewith. The base is typically made of stainless steel which advantageously provides thermal mass. Preferably the optical assembly is thermally insulating to permit the sensor, sensor base and Peltier mount to be in intimate thermal contact with the inner Peltier and thermally isolated from other components of the device.

Preferably the device is provided with a Peltier exhaust assembly which permits thermal transfer from the exhaust side of the inner Peltier to the environment.

Preferably the Peltier exhaust assembly comprises an exhaust plate positioned to allow thermal exchange with the environment. The exhaust plate is conveniently located at or near to an end of the device remote from the optical assembly. Preferably the Peltier exhaust assembly comprises means for thermally contacting the inner Peltier assembly with the exhaust plate. A thermally conducting strip may be used for this purpose (eg of copper). Preferably, the Peltier exhaust assembly comprises an exhaust guide (eg in the form of a ring) which is capable of fitting over the insulating collar of the laser module. The exhaust guide defines a slot into which the exhaust strip may be inserted.

In a preferred embodiment, the optical assembly and inner temperature controller are contained within a conducting sleeve. The conducting sleeve fulfils thermal management of the temperature sensitive components of the device eg provides a highly stable temperature environment for the inner temperature controller, provides precision temperature control for peripheral components such as the laser diode, provides a thermally stable environment for temperature control electronics and controls the temperature of incoming gases or liquids through the inlet and outlet ports. All these functions contribute to the temperature of the planar optical component being contained within desirable limits (typically the target control span is 20 micro Kelvin).

In a preferred embodiment, the conducting sleeve comprises a heat shroud which is typically made of copper. The heat shroud is preferably provided with an opening which is suitably disposed to coincide with the cavity in the optical assembly. This advantageously allows the inner Peltier assembly to be inserted in the optical assembly, after the optical assembly has been inserted in the conducting sleeve (eg heat shroud).

Preferably, the heat shroud comprises an integral laser module holder for inserting a laser module. Preferably the laser module holder is provided with an outwardly disposed insulating collar. Preferably the electronics are housed within the heat shroud.

Preferably the device comprises an outer temperature controller-which permits-coarse temperature control of for example the conducting sleeve, laser module, laser module holder, the exterior parts of the optical assembly and the electronics. The outer temperature controller is thermally independent of the inner temperature controller. The outer temperature controller conveniently takes the form of an outer Peltier assembly. Preferably, the outer Peltier assembly is provided externally of the restraining sleeve which is provided with an aperture to enable exposure of an effective area of the conducting sleeve to achieve thermal contact with the outer Peltier assembly.

Preferably, the device is provided with a means for urging the Peltier exhaust assembly onto the inner Peltier assembly. For example, a restraining sleeve is added outwardly of the heat shroud to force the Peltier exhaust assembly onto the inner Peltier assembly at one end and the exhaust plate at the other.

A preferred device of the invention is based on the principle of "a Russian doll" which has the advantage of being able to be constructed from a plurality of discrete assemblies. The assemblies of the device may be constructed as a plurality of shells which allow advantageously straightforward, sequential construction of the overall device.

Thus a preferred embodiment of the device of the invention is capable of sequential construction from a plurality of discrete assemblies, said assemblies being: an optical assembly contained within a conducting sleeve; an inner Peltier assembly comprising an inner Peltier; and a Peltier exhaust assembly, wherein: the inner Peltier assembly is housed within the cavity of the optical assembly so-as to achieve intimate thermal contact with the planar optical component and the Peltier exhaust assembly permits thermal transfer from the exhaust side of the inner Peltier to the environment and is thermally isolated from the inner Peltier assembly and conducting sleeve.

Particularly preferably, this embodiment further comprises a discrete assembly being an outer Peltier assembly in thermal contact with the conducting sleeve.

Viewed from a further aspect the present invention provides a kit capable of being assembled into a device as hereinbefore defined, said kit comprising:

an optical assembly, an inner Peltier assembly, a conducting sleeve, a Peltier exhaust assembly and an outer Peltier assembly, wherein:

the optical assembly is capable of being inserted in the conducting sleeve;

the inner Peltier assembly is capable of being housed within the cavity of the optical assembly so as to achieve intimate thermal contact with the planar optical component; the Peltier exhaust assembly is capable of being-positioned in thermal isolation from the conducting sleeve so as to permit thermal transfer from the exhaust side of the inner Peltier to the environment; and the outer Peltier assembly is capable of being positioned so as to achieve thermal contact with the conducting sleeve.

Viewed from a yet further aspect the present invention provides the use of a device or kit as hereinbefore described as a gas or liquid sensor.

Viewed from a still yet further aspect the present invention provides a process for constructing a device as hereinbefore defined comprising the steps of:

inserting an optical assembly in a conducting sleeve (eg copper heat shroud) comprising an integral laser module housing;

inserting a laser module into the laser module housing;

housing an inner Peltier assembly in the cavity of the optical assembly so as to achieve thermal contact with the planar optical component;

positioning a Peltier exhaust assembly in thermal isolation from the conducting sleeve so as to permit thermal transfer from the exhaust side of the inner Peltier to the environment.

Where appropriate, the process of the invention may comprise the additional steps of:

constructing an outer restraining sleeve;

constructing an outer casing; and positioning an outer Peltier assembly on the outer casing or restraining assembly whereby to achieve thermal contact with the conducting sleeve.

In order to impart optimum thermal performance to the device, the materials of the various component parts are judiciously chosen. Where necessary, component parts may be required to have good insulating and mechanical properties, thermal drive (good thermal conductor), thermal exhaust (good thermal conductor), high performance insulating properties and mechanical properties, high performance insulating properties, etc. Materials for these purposes will be, familiar to those skilled in the art.

The exclusion of stray radiation in accordance with the optical assembly of the device of the invention enables the number of components to be minimised and enables straightforward analysis of the signals generated by the planar optical component (such as the centre of gravity of a series of interferometric fringes for example). This is achieved by ensuring that electromagnetic radiation excites substantially only the planar optical component. The optical assembly of the device of the invention is suitable for the fault tolerant construction of planar optical sensors and ensures optimal performance from the planar optical component. Tolerances are typically reduced by approximately 1000 fold enabling cheap mass production methods such as compression moulding and injection moulding to be employed.

In a preferred embodiment, the optical assembly of the device according to the invention comprises a planar optical component having a plurality of waveguides. Typically the planar optical component comprises a sensing waveguide and a reference waveguide. Preferably the planar optical component is any of those described in WO-A-98/22807 (IMCO (1097) Ltd et al).

Preferably the optical assembly is provided with one or more seats upon which the planar optical component may be seated.

The optical assembly may comprise a holder for mounting the planar optical component and a housing adapted to receive internally said holder so as to define a longitudinal path through the device in which the planar optical component is effectively exposed in free space. Preferably the holder comprises a basal recess in which the planar optical component may be mounted. To ensure that the edge of the planar optical component which is to be excited by the electromagnetic radiation is suitably exposed in the longitudinal path, one or more longitudinal cavities may be provided in the base of the holder such that when the planar optical component is positioned adjacent an aperture in the housing, the majority of the leading and trailing edges of the planar optical component may be exposed in free space. In a particularly preferred embodiment of the invention, the holder is removably received in the housing. The provision of a holder of this type advantageously enables the planar optical component (eg sensor) to be replaced without discarding or rebuilding the supporting components. Where appropriate, the optical assembly of the device of the invention may provide a means for providing a constant force between the holder and the housing.

Preferably the optical assembly of the device of the invention includes a guiding means in the form of a spacer incorporated in the planar optical component or in the main body of the optical assembly. In the first instance, the spacer may be incorporated in the planar optical component conventionally during manufacture. In the second instance, the spacer takes the form of (or is located on) a seat in the optical assembly upon which the planar optical component is located in use. This latter embodiment has the advantages that the sensing layer of the planar optical component is more efficiently exposed to the test material, that the manufacture of the planar optical component is simplified and that the disturbance of the planar optical component (as a result of bringing it into contact with the seat or with the modified seat upon which the spacer is located) is minimised. The material from which the spacer is made is judiciously chosen in terms of refractive index and physical properties. The spacer is advantageously permeable to the sample under analysis.

In a preferred embodiment, the optical assembly of the device of the invention comprises a first aperture at a first end of a longitudinal path for admitting electromagnetic radiation and a second aperture at a second end of said longitudinal path for transmitting electromagnetic radiation. Provided the spacer is of a known predetermined thickness relative to the known distance between the first aperture and the surface upon which the planar optical component is seated within the optical assembly, electromagnetic radiation may be effectively guided onto the waveguides.

In a particularly preferred embodiment, the planar optical component and incorporated spacer may be located on a silicon baseplate. The silicon baseplate which is typically optically flat may be conveniently provided with a hole over which the planar optical component is located. Conveniently, the spacer may seal the hole in the baseplate provided the spacer is sufficiently (eg optically) flat.

In an especially preferred embodiment, the silicon baseplate is provided with a channel (eg a V-shaped channel) capable of receiving an optical fibre wherein the depth of the channel predetermines the position and height that electromagnetic radiation is emitted relative to the surface of the silicon baseplate. Since the position of the waveguides above the surface of the silicon baseplate is determined by the height of the incorporated spacer, the position of the electromagnetic radiation and the waveguides may be correlated. Stray light is simply emitted into the silicon.

In an alternative especially preferred embodiment, the silicon baseplate forms part of an integrated electro-optic device in which a laser source is integrated into the silicon baseplate. The guiding means is provided by an incorporated spacer located on the silicon baseplate or the planar optical component as hereinbefore described.

In either of the especially preferred embodiments, the output may be monitored by a discrete detector or an imaging fibre or fibre array may be used to collect the output image. Alternatively, a photodetector could be integrated into the silicon structure. Using fibres in and out is very useful in safety critical applications (ie there is no electricity).

Preferably, the optical assembly of the device of the invention comprises means (eg a flat surface, one or more seats or seals) for providing a gas or liquid seal to the surface of the planar optical component to allow transport of an analyte to and from the planar optical component (eg sensor) and measurement of the optical behaviour of the component in the presence of the analyte. The provision of a seal to the surface of the planar optical component (eg sensor) reduces the dead volume to a minimum (this is important in providing optimal performance with chemical sensors). The provision of a seal to the surface of the planar optical component (eg sensor) also enables liquid samples to be used in addition to gas samples. This is not conceivable with a conventional freestanding arrangement as wetting of the end faces would lead to optical misalignment.

Preferably, the optical assembly of the device of the invention is capable of mounting an electromagnetic radiation source such as a laser. Preferably, the optical assembly is capable of mounting an electromagnetic radiation detection device (eg photodiode array). Preferably, the optical assembly of the device of the invention comprises means for the provision of removable or non-removable components between the planar optical component (eg chemical sensor) and a source of electromagnetic radiation and/or between the planar optical component and a radiation detection device. Such components may be conventional lenses, polarisers, electromagnetic radiation windows, spacers, window/spacer retainers, etc mounted in a conventional manner.

In all cases, the body of the optical assembly is preferably opaque to minimise stray electromagnetic radiation. Thus the planar optical component may be advantageously mounted on a base which does not transmit electromagnetic radiation, thereby preventing stray electromagnetic radiation passing thereunder. Preferably, the seat or seal of the optical assembly also may not transmit electromagnetic radiation in the longitudinal direction whereby to further prevent stray electromagnetic radiation passing over the sensor surface and reaching the detector. Preferably, the seat or seal has an inlet, a channel and an outlet providing a means through which analyte (eg gases or liquids) may pass. In this way, analyte is able to pass into and out of the absorbent layers of a planar optical component (eg chemical sensor) leading to measurable changes in the output electromagnetic radiation. Preferably, the extremes (edges) of the sensor are sealed from the environment to prevent extraneous effects from gases, vapours or liquids from external sources not related to the sample under analysis.

In a preferred embodiment, where the device of the invention is to be used on test materials, it is preferred that the thermal mass of the incoming material is minimised by ensuring the sample volume and the inlet volume are minimised. This may be achieved by low dead volume within the sensor "cavity" and narrow bore inlets. In addition, the thermal mass of the inlet system needs to be high to prevent thermal fluctuation over time. Stainless steel pipework is preferred. Preferably, the inlet pipe is in thermal contact with the copper shroud eg the pipework is run along the shroud. Appropriate thermal lagging of the pipework may be required in order to prevent too high a thermal loss from the complete outer system.

The invention will now be described in preferred embodiments in a non-limitative sense with reference to the accompanying Figures in which:

FIG. 4 illustrates an exploded view of a cross-section of an optical assembly of a disassembled embodiment of the invention;

Figure 1:
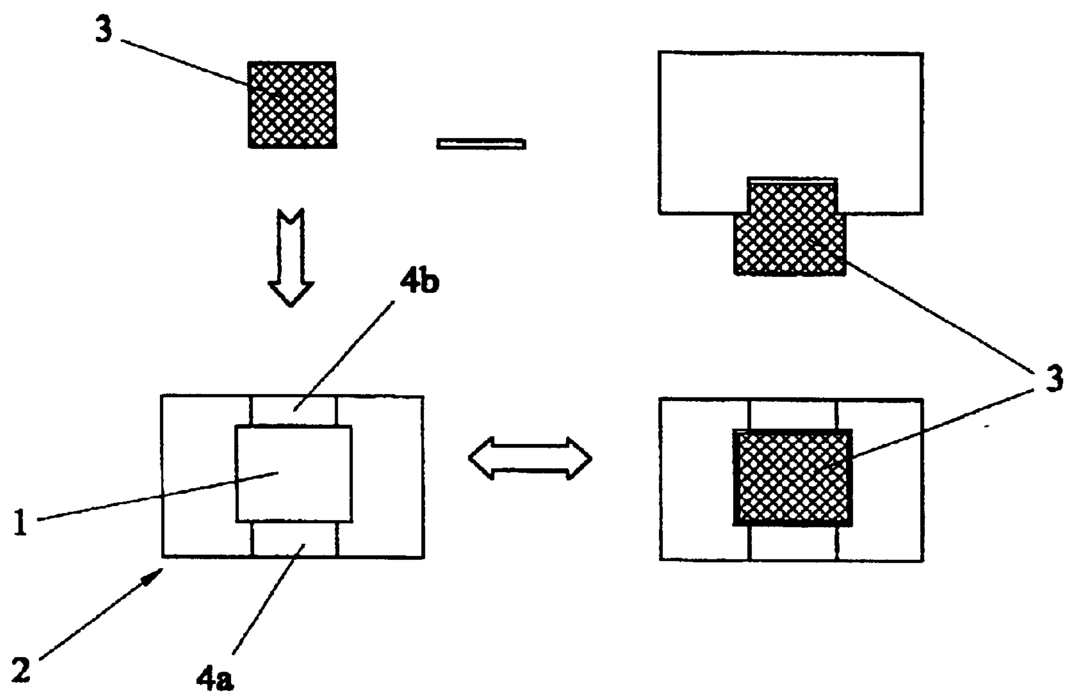
FIG. 1 illustrates a bottom view of a holder of an optical assembly in accordance with an embodiment of the invention.

FIG. 1 illustrates a holder 2 in which a planar optical component (sensor) 3 is mounted in a basal recess 1. Longitudinal cavities 4*a* and 4*b* are provided along a longitudinal path to allow the sensor to be positioned adjacent an aperture in a housing (of the type shown in FIGS. 2 and 5) so as to ensure that the majority of the leading and trailing edges of the sensor are exposed in free space.

Figure 2:
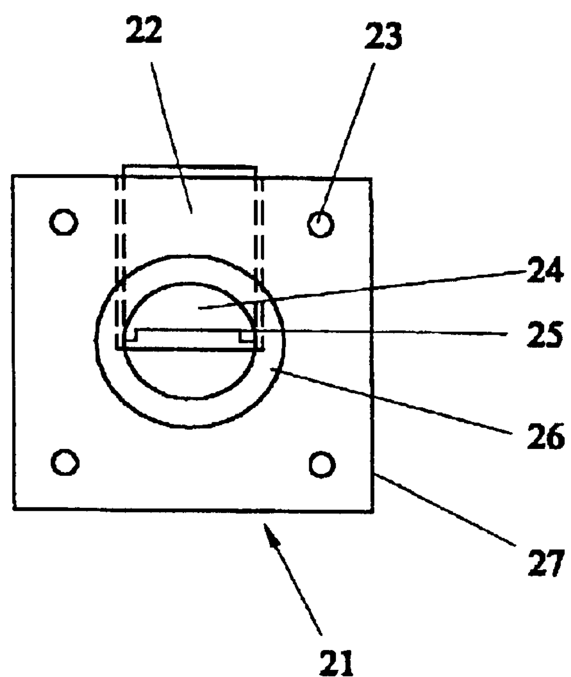
FIG. 2 illustrates an end elevation of a holder positioned within a housing of an optical assembly in accordance with an embodiment the invention.

FIG. 2 shows an end elevation of the optical assembly 21 of a device of the invention with a holder 22 positioned within a housing 27 in such a manner as to define a longitudinal path into the housing, through to a planar waveguide chemical sensor 25 and out of the housing 27 (not shown). The end face of the housing 27 has dowel holes (one of four is designated with numeral 23) to enable the reliable and accurate location of additional plates upon which may be mounted electromagnetic radiation sources (such as a laser diode for example), electromagnetic radiation detectors (such as a photodiode array for example) and other optional components such as lenses. The housing has a circular aperture 24 which allows the electromagnetic radiation to pass therethrough (to the planar waveguide chemical sensor 25). The aperture 24 also has a recess 26 which enables a window capable of transmitting the electromagnetic radiation to be fitted. This ensures that the sensor 25 is sealed from the surroundings in terms of potential chemical interference. A means for transporting the analyte to the sensor has been omitted from this Figure for the sake of clarity but is described in detail hereinafter.

Figure 3:
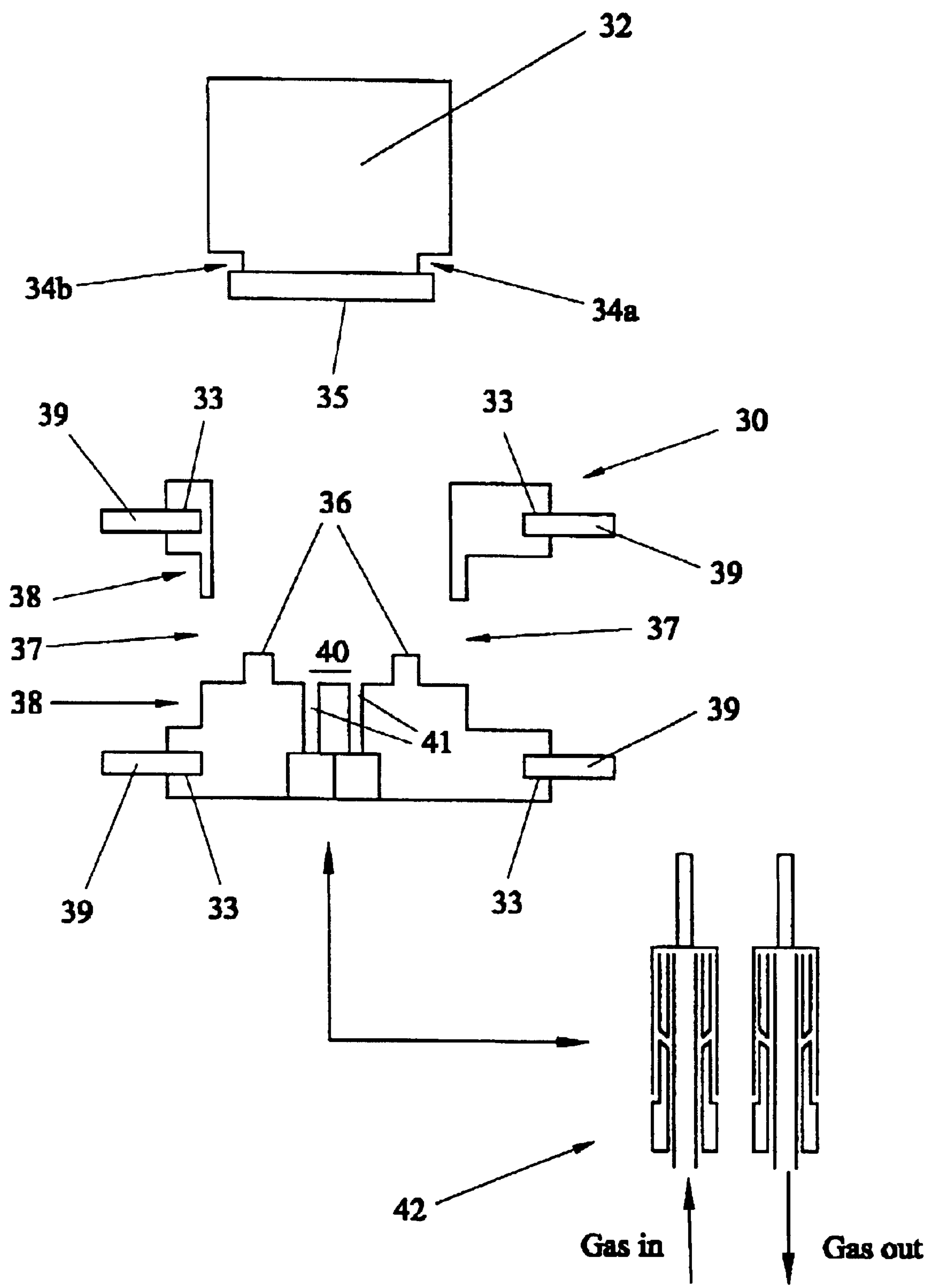
FIG. 3 illustrates a cross-sectional disassembled view of an optical assembly of an embodiment of the invention.

An exploded cross-section of the optical assembly of an embodiment of the device of the invention is provided in FIG. 3. Shown removed from the housing 30 are the sensor holder 32 and sensor 35 with longitudinal cavities 34*a* and 34*b* allowing the majority of the leading and trailing edges of the sensor to be exposed in free space. The sensor 35 is inserted into the housing 30 such that the top surface of the sensor 35 makes contact and seals (in a gas/liquid type manner) with the sensor housing seat 36. The apertures 37 for the passage of electromagnetic radiation and the recesses for the windows 38 allow the transmission of electromagnetic radiation. The windows themselves have been omitted for the sake of clarity. The dowel holes 33 are shown occupied by dowels 39. The channel 40 for the passage of analyte over the surface and the conduits 41 for the transmission of the analyte to and from the sensor surface are shown. In this embodiment, the conduits 41 are terminated with ¼"28 UNF inverted cone fittings (made by OMNIFIT) 42 to provide a mechanical connection to the desired test source.

FIG. 4 shows in detailed cross-section the optical assembly of an embodiment of the invention. The holder 32 and sensor 35 are shown separately in FIG. 4*i*. The housing is shown separately in FIG. 4*iii* with windows 43 and a plate mounted with a laser diode 44 and a plate mounted with a photodetector array 45. The precise location of the plates is achieved by the dowels 39. The housing seat 36, the channel for test materials 40 and the conduits 41 are as hereinbefore described. FIG. 4*ii* shows the complete assembly with the holder 32 and sensor 35 in place in the housing 30. The positioning of holder 32-in housing 30 creates a dead volume 40. The volume around the ends of the sensor 46 is minimised to reduce effects due to external or ambient chemical changes. FIG. 4*iii* shows the inverted cone fittings for connection to the device of the invention and transmission of analyte.

Figure 5I:
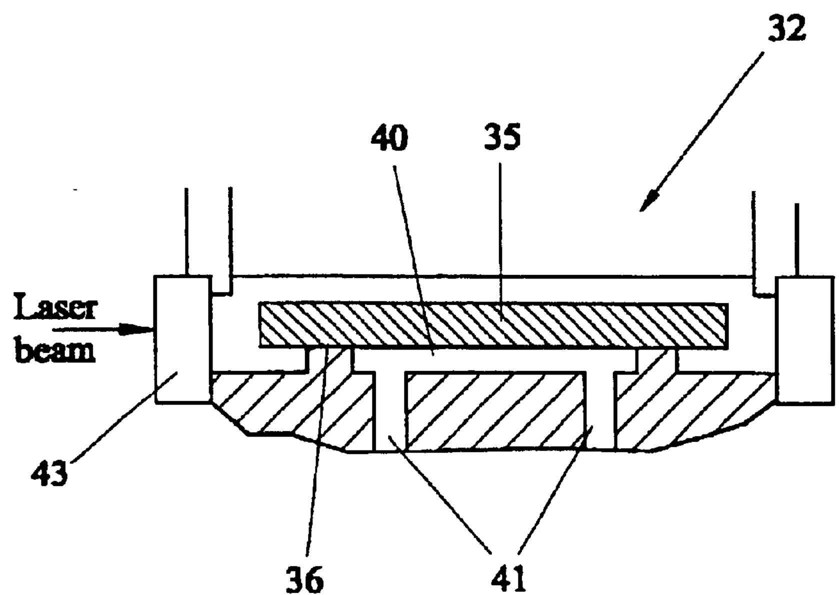
FIG. 5 illustrates a top view of a housing and a partial side view of a holder within the housing of an optical assembly in accordance with an embodiment of the invention.
Figure 5:
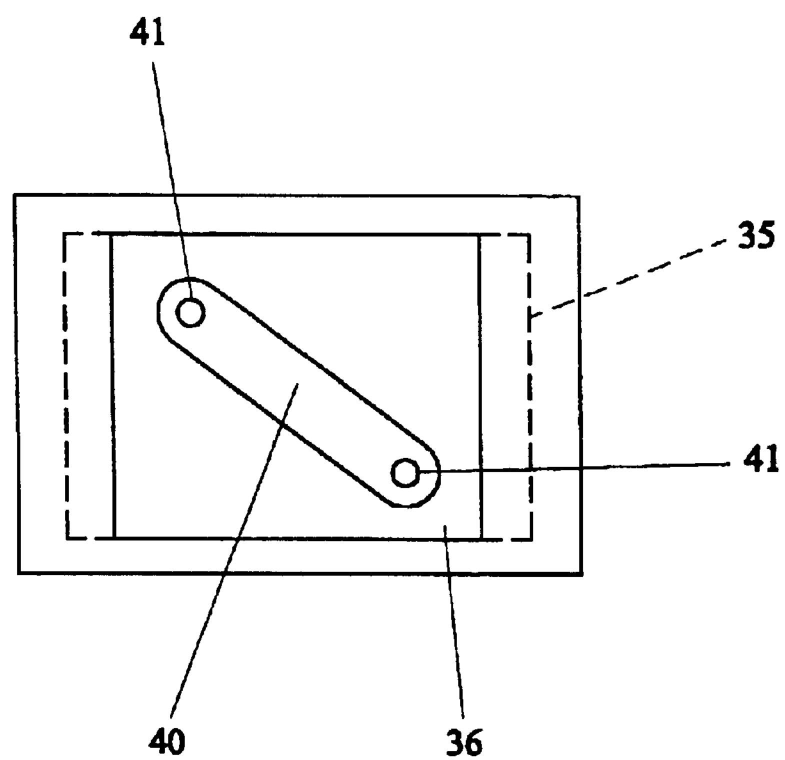

FIGS. 5*i* and 5*ii* show a partial cross-section and plan view respectively of the sensor housing seat which seals to the surface of the sensor 35. The seat or seal 36 provides a complete gas tight seal to the surface of the sensor 35. The conduits 41 allow the passage of test analyte to and from the sensor surface via the channel 40 which allows the analyte to come into intimate contact with the sensor surface.

Figure 6:
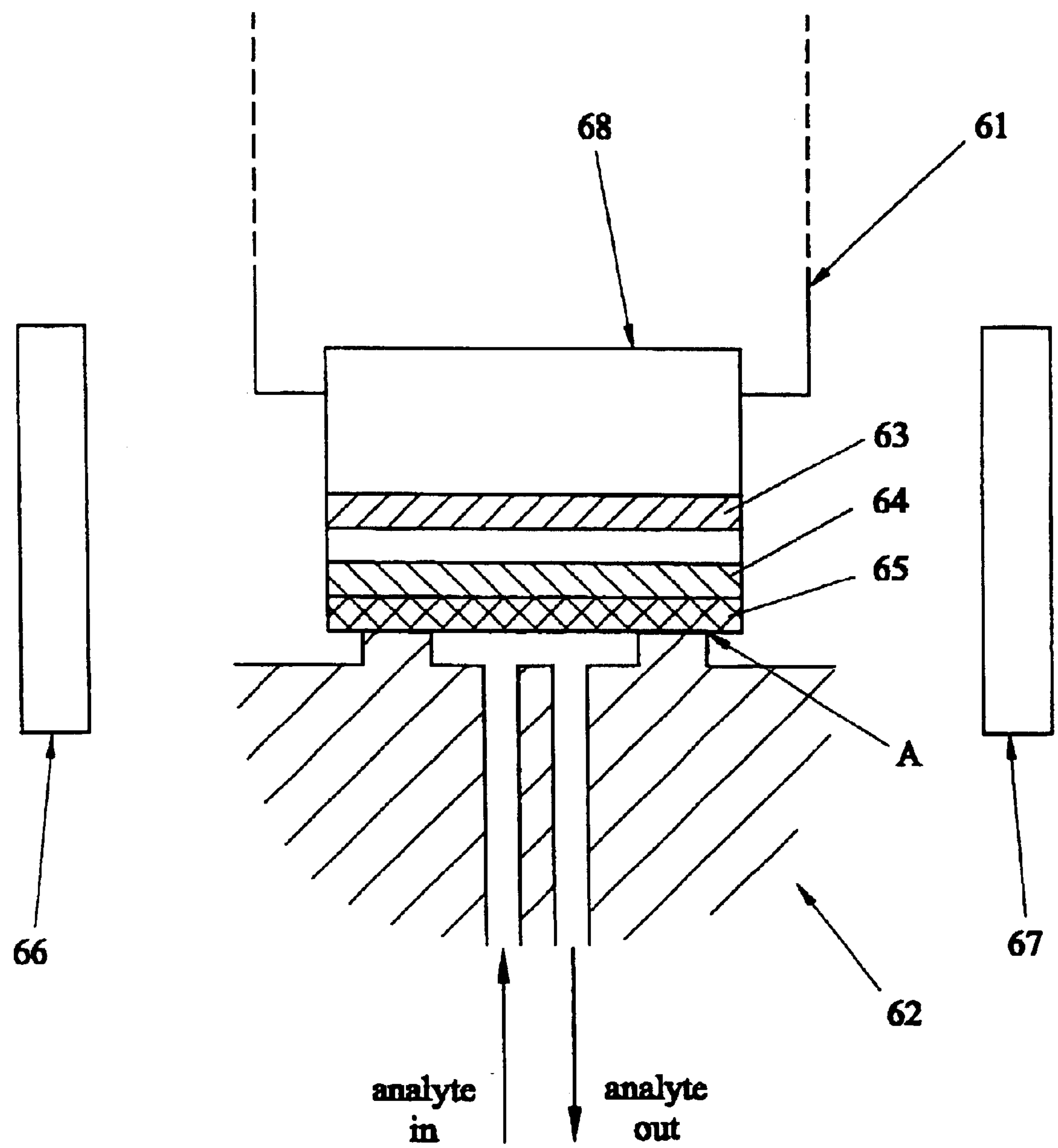
FIG. 6 illustrates an optical assembly of an embodiment of the invention.

FIG. 6 illustrates an assembled holder 61 and housing 62 of an optical assembly of a device of the invention. The sensor 68 comprises waveguides 63 and 64 together with a spacer 65 which may be deposited when the sensor is manufactured. Provided the spacer thickness and height of surface A are known relative to the position of electromagnetic radiation source 66, the electromagnetic radiation will fall substantially wholly on the waveguides. The holder and housing are made opaque to the wavelength of electromagnetic radiation to reduce stray output to the detector 67. Engineering tolerances are around 200 $\mu$m.

Figure 9:
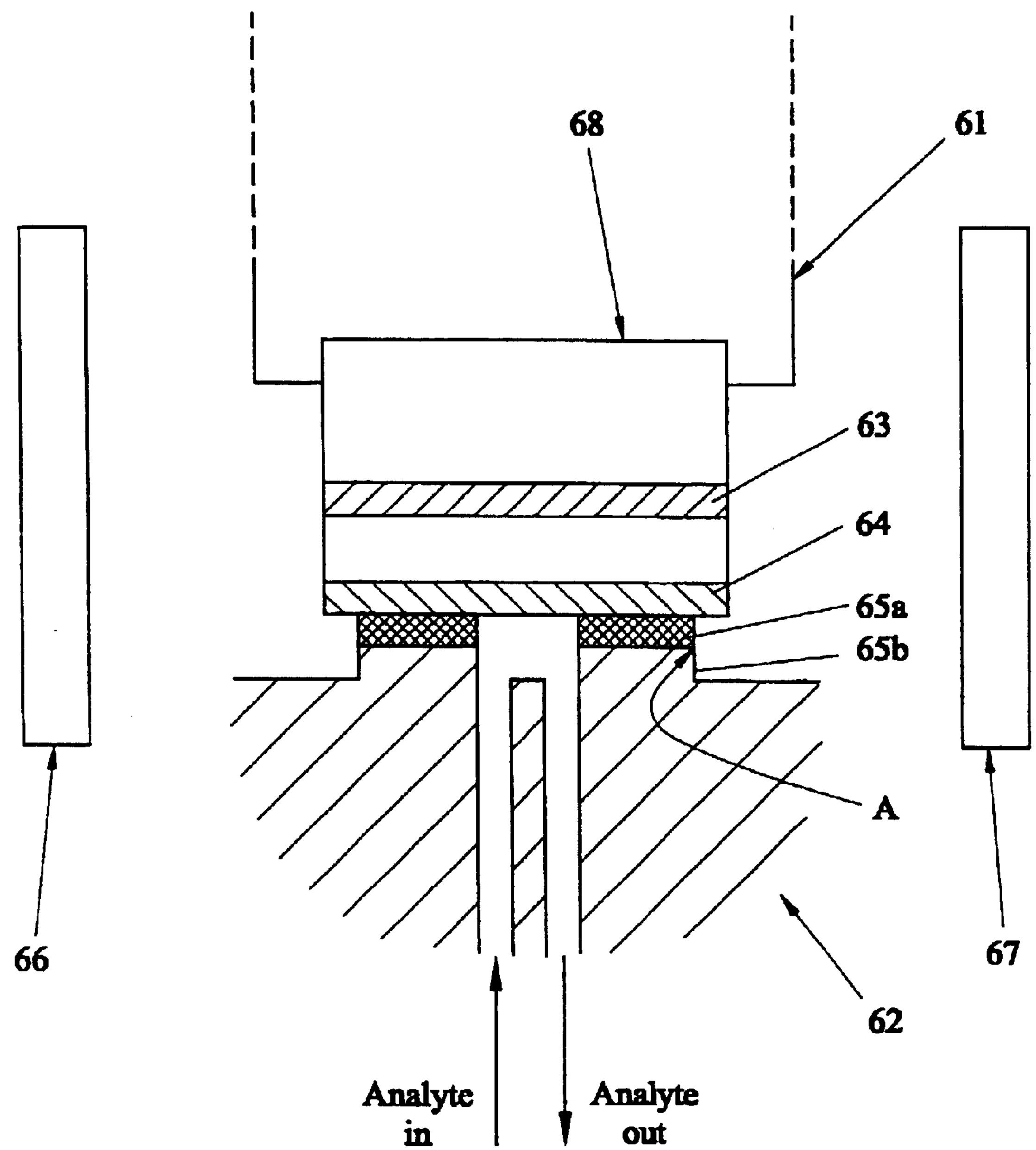
FIG. 9 illustrates an optical assembly of a further embodiment of the invention.

FIG. 9 illustrates an assembled holder 61 and housing 62 similar to FIG. 6 but with the spacer 65*a* provided on the seats 65*b*. This improves the exposure of the sensing layer to test material.

Figure 7:
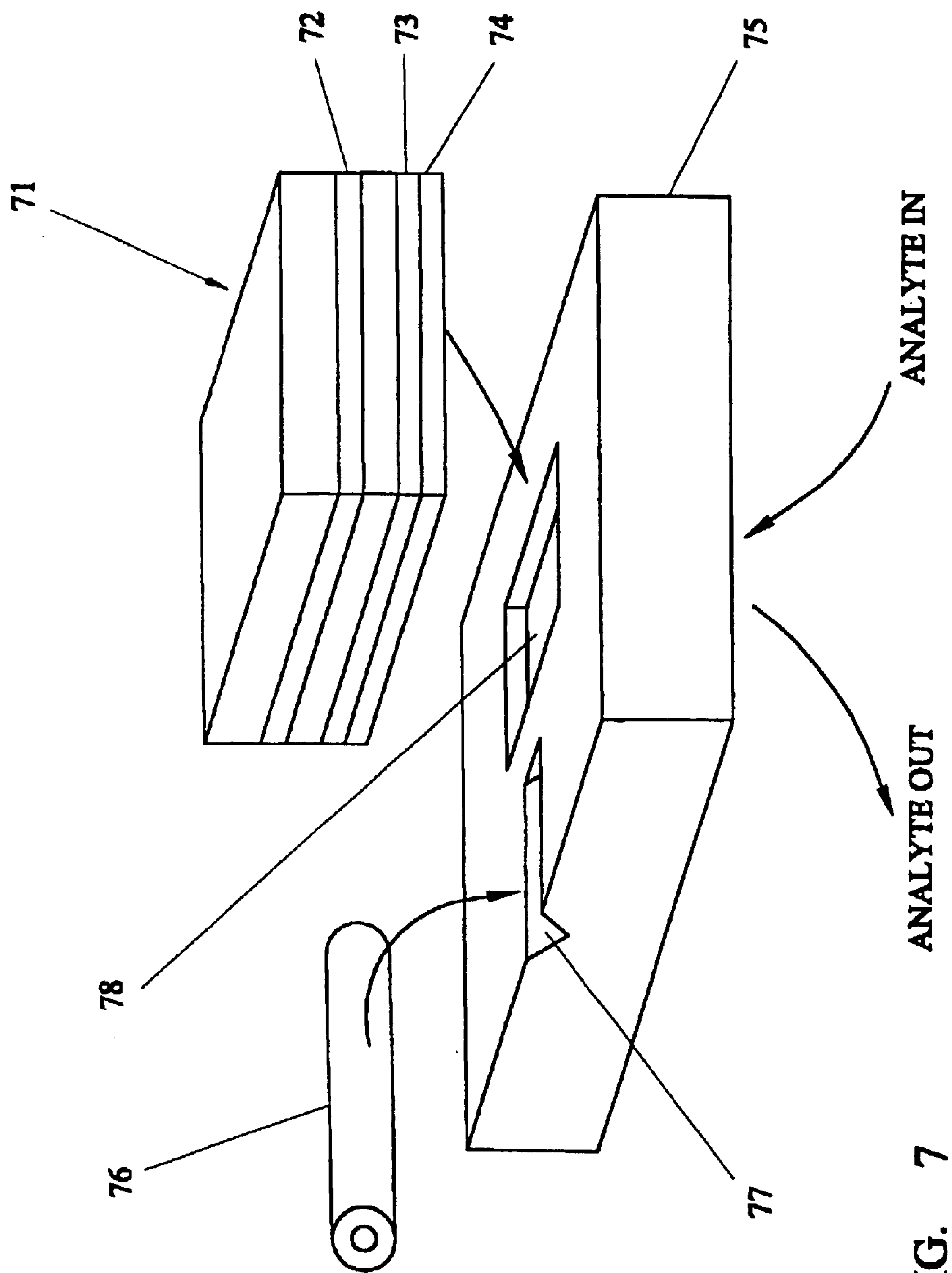
FIG. 7 illustrates an optical assembly of a further embodiment of the invention.

In the embodiment of FIG. 7, the sensor 71 is provided with reference and sensing waveguides (72 and 73), spacer 74 and a silicon baseplate 75. Optical fibre 76 is located in a V-groove 77 of baseplate 75. The position and height of the emitted light relative to the silicon baseplate is determined by the V-groove. The baseplate has hole 78 etched in it over which the sensor is located. The height of the waveguide relative to light from the fibre is set by the spacer which additionally seals the hole 78 by being sufficiently flat. Stray light is emitted into the silicon. A discrete detector may be used to monitor output or an imaging fibre or fibre array may be used to collect output images, or a detector system may be incorporated (integrated) in the baseplate.

Figure 8:
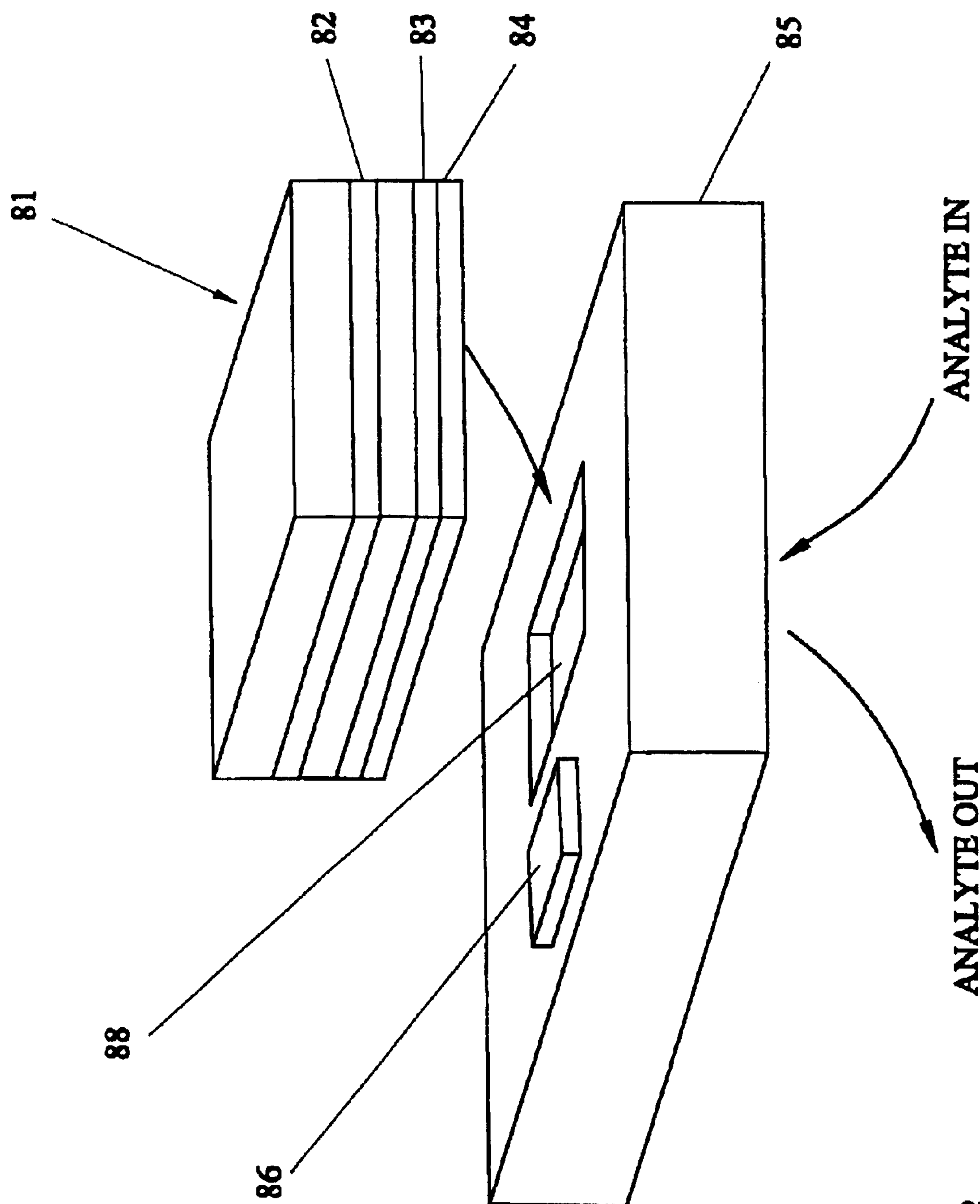
FIG. 8 illustrates an optical assembly of a further embodiment of the invention.

In the embodiment of FIG. 8, the sensor 81 of the optical assembly is provided with reference and sensing waveguides 82 and 83, a spacer 84 and a silicon baseplate 85. Laser 86 is integrally located in the silicon baseplate. Thus, this embodiment represents an integrated electro-optic device in which the laser source 86 is integrated in the silicon baseplate. Output may be discrete, integrated or fibre optic as described hereinbefore.

FIGS. 10 to 18 are intended to illustrate in detail the various components and stages of construction of a preferred embodiment of a device of the invention. The materials of the various components have been tailored to provide optimum thermal performance and will be described hereinafter and (in particular) with reference to the key to FIG. 18.

Figure 10:
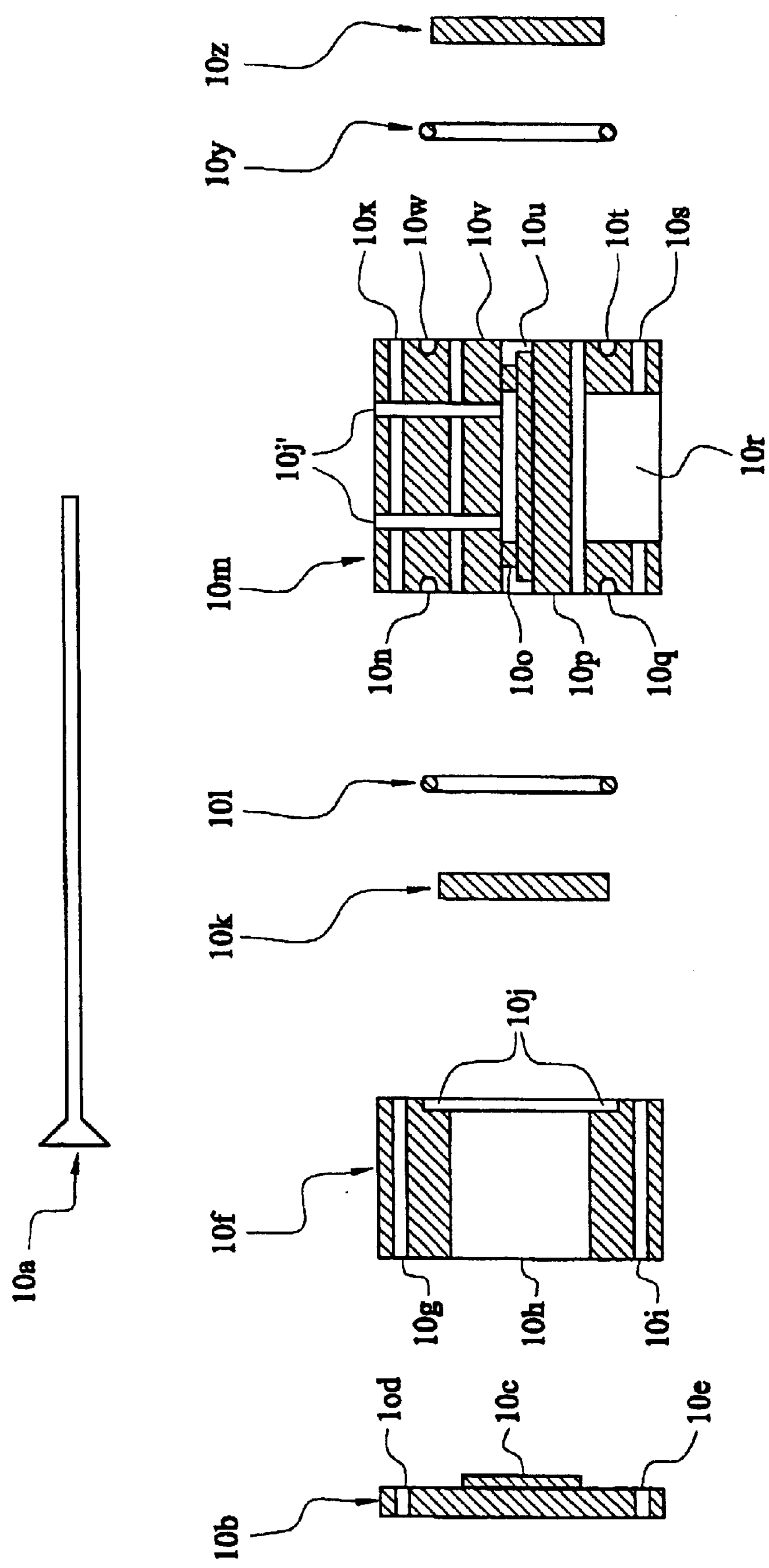
FIGS. 10 to 18 illustrate the components and stages of construction of an embodiment of the device of the invention.

FIG. 10 illustrates an optical assembly of a preferred embodiment of the invention. This is similar to those optical assemblies illustrated in FIGS. 1 to 9 except that the holder and housing are integral to the main body of the optical assembly (10*m*) rather than being separable parts.

Outer part (10*b*) comprises a mounting plate (10*d*) made of a suitable engineering material with good insulating properties which has locating holes (10*e*) for long reach countersink bolts (10*a*) and a photodiode array (10*c*). A spacer/window retainer (10*f*) made of the same engineering material comprises locating holes (10*g* and 10*i*) for the bolts (10*a*) and a broad aperture (10*h*) to allow output light from the sensor to reach the photodiode (10*c*). A recess (10*j*) retains a window (10*k*) in the correct position during assembly. The window (10*k*) is made of 4 mm thick quartz and is sealed to the main body by an o-ring (101) which may be constructed of Viton or a higher performance elastomer which is held in a seat (10*n* and 10*q*) on the exit face of the main body (10*m*) of the optical assembly.

The main body (10*m*) is made of a high performance insulating material which has good mechanical strength and is readily machineable. An example of such a material is Duratec 750. Locating holes (10*x* and 10*s*) are provided for the long reach bolts (10*a*) and the sensor is held in position by two stainless steel part cylinders (10*p* and 10*v*). The upper part cylinder (10*v*) is threaded to accept the inlet and outlet pipework (not shown) which pass through the main body at inlet/outlet conduits (10*j*'). Access to the surface of the sensor (10*u*) is possible by virtue of the void created between the upper part cylinder (10*v*) and the sensor (10*u*) by an intervening gasket (10*o*). This is made of a high performance (in terms of chemical resistance and low absorbance) polymer such as Viton. The sensor is mounted on a part cylindrical sensor base (10*p*) which is made of stainless steel. A cavity (10*r*) exposes the rear face of the sensor base (10*p*) to enable subsequent construction of the inner Peltier assembly (described hereinafter). The entry face of the main body (10*m*) contains an o-ring seat (10*t* and 10*w*) on which an o-ring (10*y*) mounts to provide a seal with an input window (10*z*) in the form of a 4 mm quartz construction.

Long reach countersink bolts (10*a*) inserted in the locating holes 10*d*, 10*e*, 10*g*, 10*i*, 10*x* and 10*s* and into the copper shroud (not shown) assist in holding the optical assembly together. They may be made of steel for high-pressure applications or of nylon (which is advantageous from the thermal management perspective) where demanding pressure specifications are not required.

Figure 11:
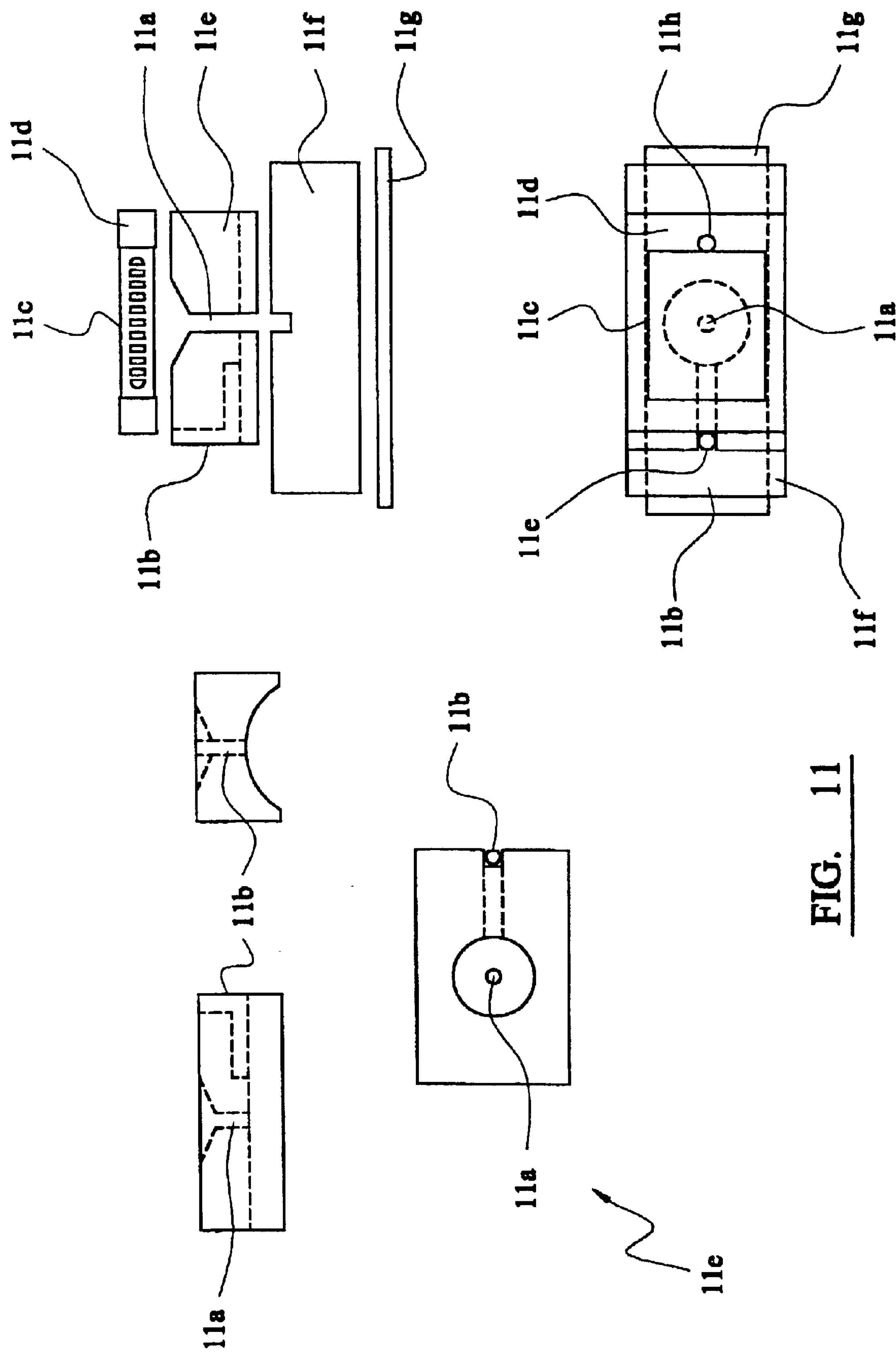

FIG. 11 shows the components of the inner Peltier assembly of a preferred embodiment of the invention. This comprises an inner Peltier mount (11*e*) which is made of a good conducting material (eg copper—if it is electrochemically compatible with stainless steel with regard to corrosion) which may be fixed (11*a*) to the sensor base (11*f*) which is in intimate thermal contact with the sensor (11*g*). The inner Peltier mount (11*e*) is adapted to receive a locating countersink bolt (11*a*) which enables it to be bolted to the sensor base (11*f* and see reference 10*p* in FIG. 10). The inner Peltier mount (11*e*) has a concave underside in order to make optimum thermal contact with the sensor base and a channel (11*b*) to provide a mounting point for a 2 mm thermistor. An inner Peltier (11*c*) is mounted directly on the inner Peltier mount (11*e*) and is insulated by a surround (11*d*). The surround (11*d*) may be made of a foam type material or mechanically sound insulating material as desired. Parts (11*d*), (11*c*) and (11*e*) may be bonded with an appropriate thermally conducting adhesive if desired.

The inner Peltier assembly is also shown in plan view in FIG. 11 with the Peltier lead out (11*h*). It is important to insulate the thermistor from the inner Peltier (11*c*) and to separate the thermistor and Peltier wires whilst they are in close proximity to the inner Peltier itself.

The sensor (11*g*) and sensor base (11*f*) are located in the main body of the optical assembly which is bolted into a copper heat shroud (described hereinafter). The inner Peltier assembly is generally constructed within the cavity of the optical assembly which exposes the sensor base. A jig may be required to construct parts (11*e*), (11*c*) and (11*d*) and to route the inner Peltier and thermistor wiring prior to placement in the cavity of the optical assembly.

Figure 12:
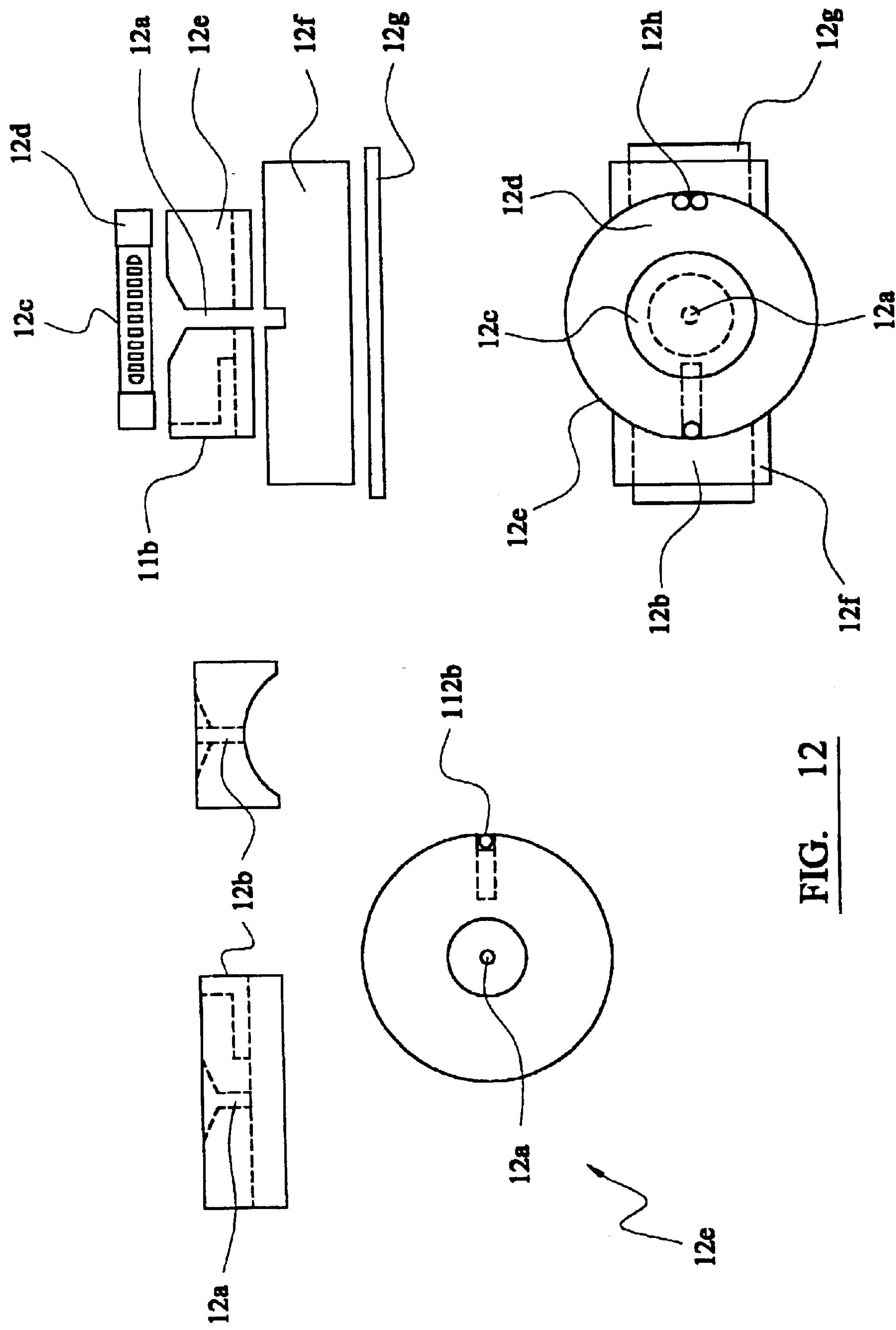

FIG. 12 illustrates a circular embodiment corresponding to the square embodiment shown in FIG. 11. This is a simpler machining proposition and it will be appreciated that where square apertures are depicted in other Figures, circular may be equally appropriate.

Figure 13:
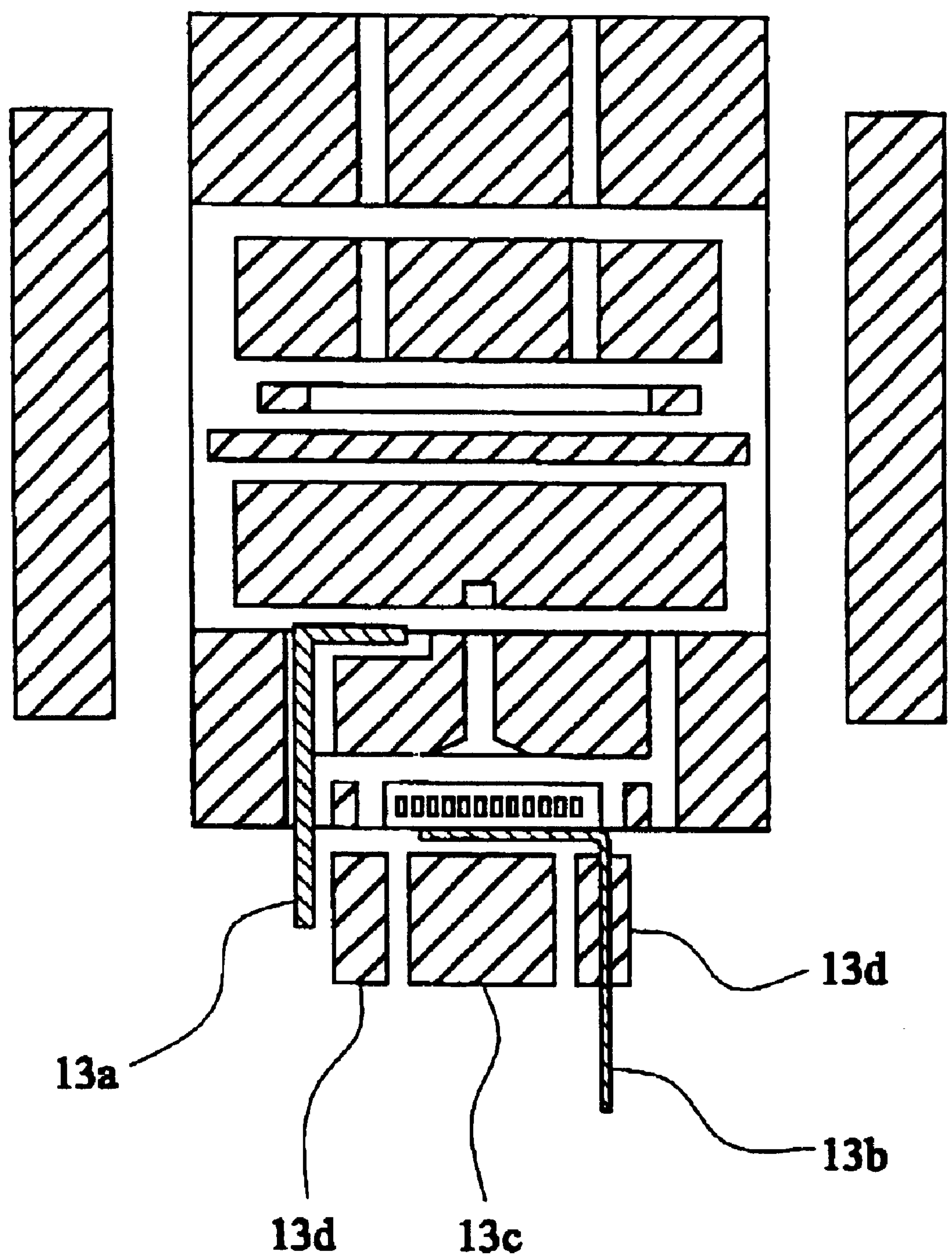

FIG. 13 illustrates schematically a cross sectional side elevation of an optical assembly and inner Peltier assembly. Peltier wiring (13*b*) and a thermistor (13*a*) are shown. In addition, a part of the Peltier exhaust assembly (13*c*) and the attendant insulation (13*d*) are shown. These are described in greater detail hereinafter.

Figures 14A, 14B, 14C:
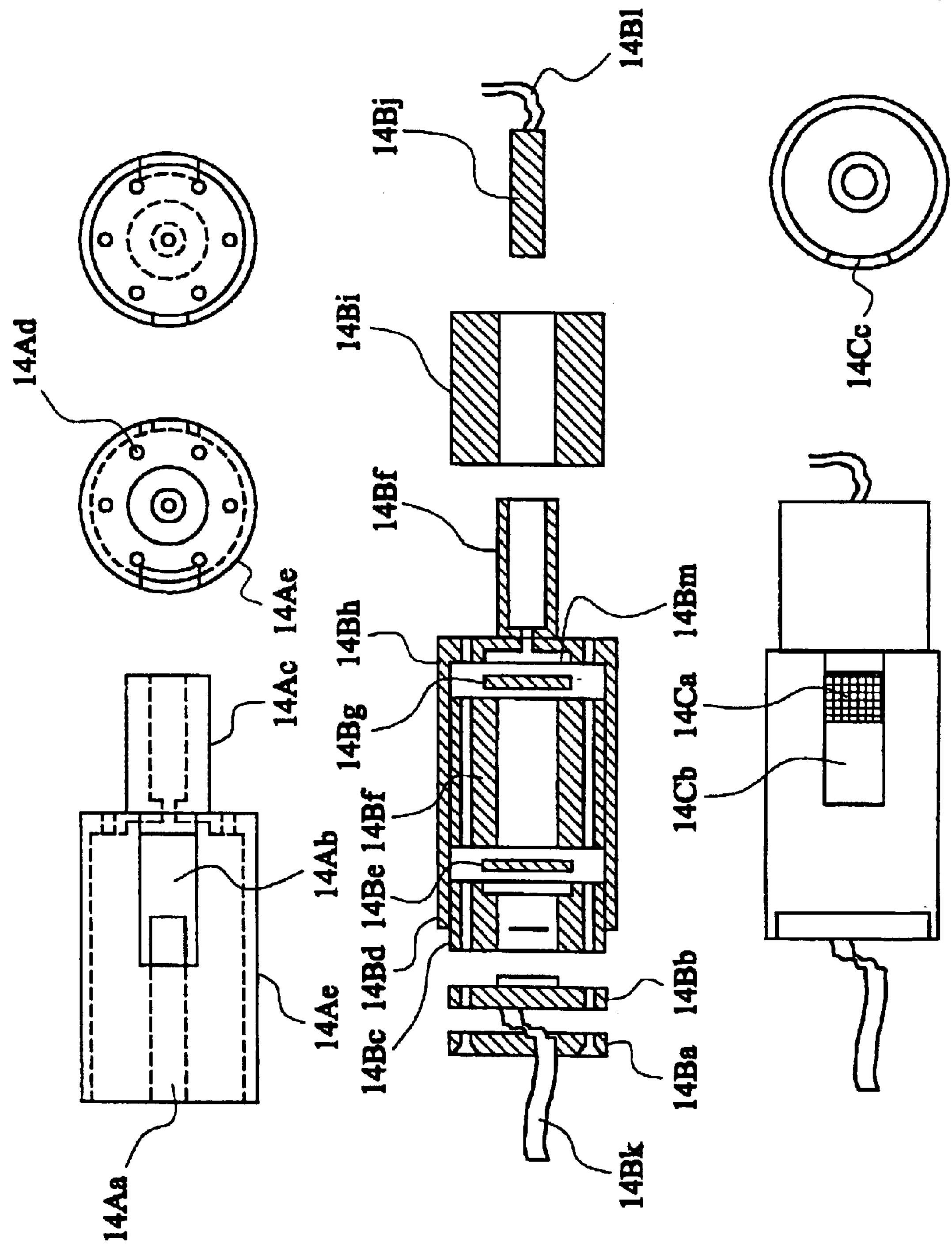

FIG. 14A illustrates a heat shroud (14Ae) and integral laser module holder (14Ac). During the initial construction stage, slot (14Aa) allows the optical assembly to slide into the heat shroud without interfering with the inlet and outlet pipes. If the pipes are easily removable, the slot may be replaced with one or more appropriately positioned access holes. An opening (14Ab) and associated slot allow access to the cavity of the optical assembly (see FIG. 10 reference r) into which the inner Peltier assembly is placed in a subsequent construction stage.

The laser module is mounted (in the next stage of construction) in the laser module holder (14Ac) at one end of the heat shroud (14Ae). The outer diameter of the laser module holder (14Ac) is designed to be equal to that of the inner diameter of the main body of the optical assembly (FIG. 10 reference m). Thus the machining of the high performance insulator can be used to insulate the laser module holder too. The end elevation shows details of the slot and the six tapped holes (14Ad) in which the long reach countersunk bolts (FIG. 10 reference a) are located to hold the optical assembly together.

FIG. 14B illustrates an exploded view of the optical assembly with the laser module holder, laser module and heat shroud. The optical assembly comprises a photodiode and mount (14Bb), spacer/window retainer (14Bc), window (14Be), o-ring (omitted for clarity), main body (14Bf) (detail omitted for clarity), o-ring (omitted for clarity) and window (14Bg) which locates in recess (14Bm). A conducting plate (14Ba) retains the components of the optical assembly in place within the copper heat shroud (14Bh) with the assistance of long reach countersink bolts which have been omitted for clarity.

The laser module (14Bj) may be secured with two Allen bolts and is close fitting into the laser module holder (14Bp). An insulating collar (14Bi) is placed over the laser module holder (14Bp). The ribbon cable output of the photodiode array (14Bk) and the two-core output of the laser module (14Bl) are also shown for the sake of completeness.

FIG. 14C illustrates the constructed optical assembly and heat shroud in both side and end elevation. Internal detail has been largely omitted for clarity. A section of the main body of the optical assembly (reference Bf in FIG. 14B) is clearly visible (14Ca), as is the majority of the sensor base (FIG. 10 reference p) which is exposed by opening (14Cb).

Figures 15A, 15B, 15C:
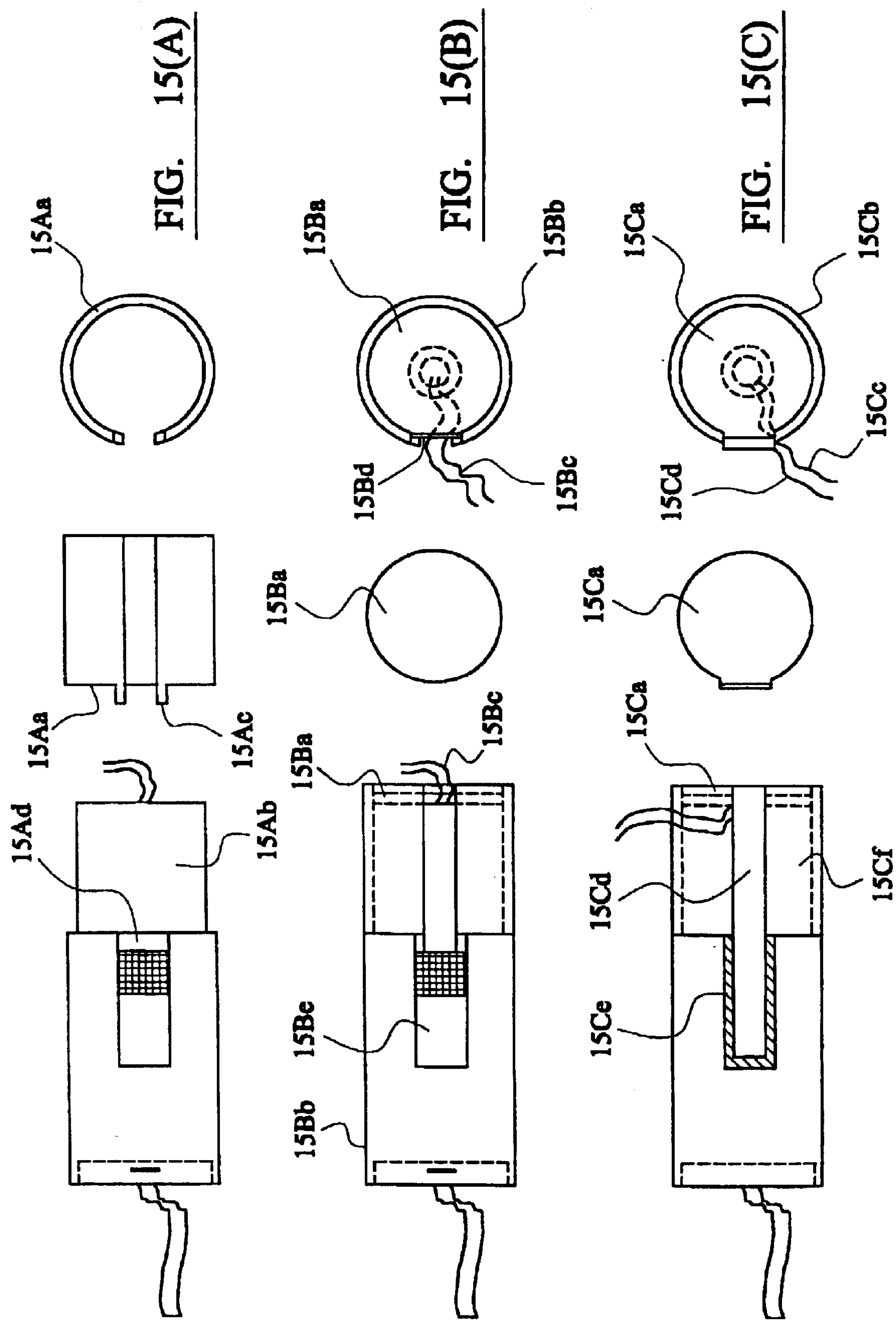

The next stage of construction involves fitting the Peltier exhaust assembly as illustrated in FIGS. 15A–C. Thus Peltier exhaust guide (15Aa) in the form of a ring made of an insulating engineering material fits over the insulating collar of the laser module (15Ab) and comprises locating lugs (15Ac) which fit into the exhaust slot (15Ad). As illustrated in FIG. 15B, an insulating plate (15Ba) is fitted into the construction (15Bb) to isolate the laser module and its lead outs (15Bc) and the heat shroud from the Peltier exhaust assembly.

At this stage, the inner Peltier assembly is located in the cavity of the optical assembly in thermal contact with the sensor base. Thus the inner Peltier mount, inner Peltier, insulating surround (FIGS. 11 and 12 references c, d and e) and a conducting block (15Bd) it required to bring the assembly up to the appropriate level to be inserted into the cavity of the optical assembly (15Be) as described hereinbefore.

An exhaust strip (15Cd) of copper or an equivalent material is laid in a slot created by the exhaust guide (15Cf) and a mechanically rigid insulator (15Ce) (made of Duratec 750 or an equivalent material). The exhaust strip makes good thermal contact with the inner Peltier assembly beneath it (not shown for clarity) and the exhaust plate (15Ca) which is inserted in the end of the construction. The laser module lead-outs (15Cc) are brought-around the exhaust strip (15Cd).

In FIG. 16, a restraining sleeve is shown in side and end elevation. The primary purpose of the restraining sleeve is to restrain and force the Peltier exhaust assembly on to the inner Peltier assembly at one end and the exhaust plate at the other. At the same time, it may usefully provide cable conduits for the laser module, inner Peltier assembly and the thermistor. In principle, the outer casing (see FIG. 18) could perform the function of the restraining sleeve. However the ease of construction may be compromised and so a separate sleeve is preferred.

Figure 16A:
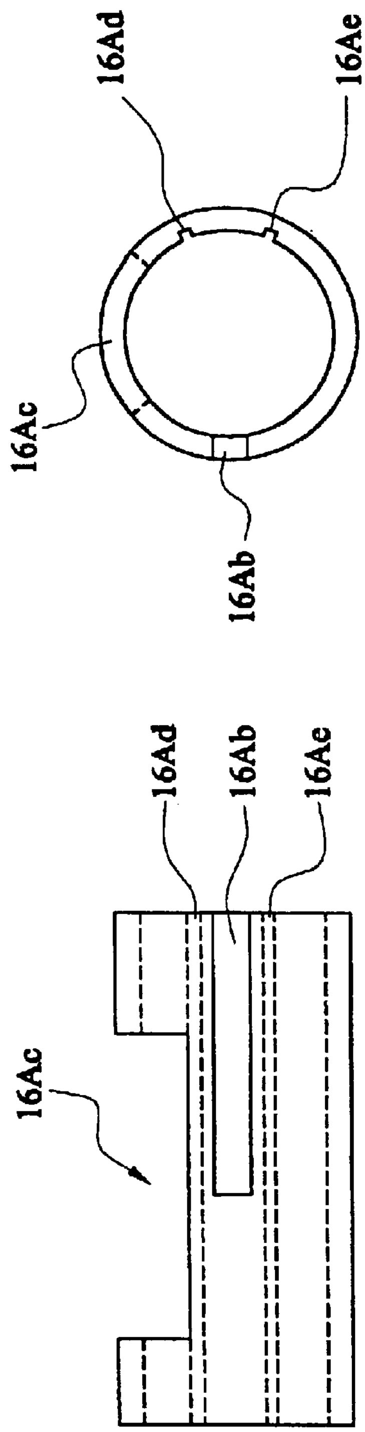

In FIG. 16A, the restraining sleeve is constructed of an insulating engineering material. The aperture (16Ac) provides exposure of a wide area of the copper shroud for thermal contact to an outer Peltier assembly. The slot (16Ab) allows the sleeve to slide over the optical assembly. As with the copper shroud, this may be replaced by one or more holes if the input and output pipes are easily detachable from the optical assembly. Slots (16Ad and 16Ae) provide two cable conduits. This allows the potentially hot leads of the inner Peltier to be routed separately from the thermally passive thermistor and laser module lead-outs.

Figure 16B:
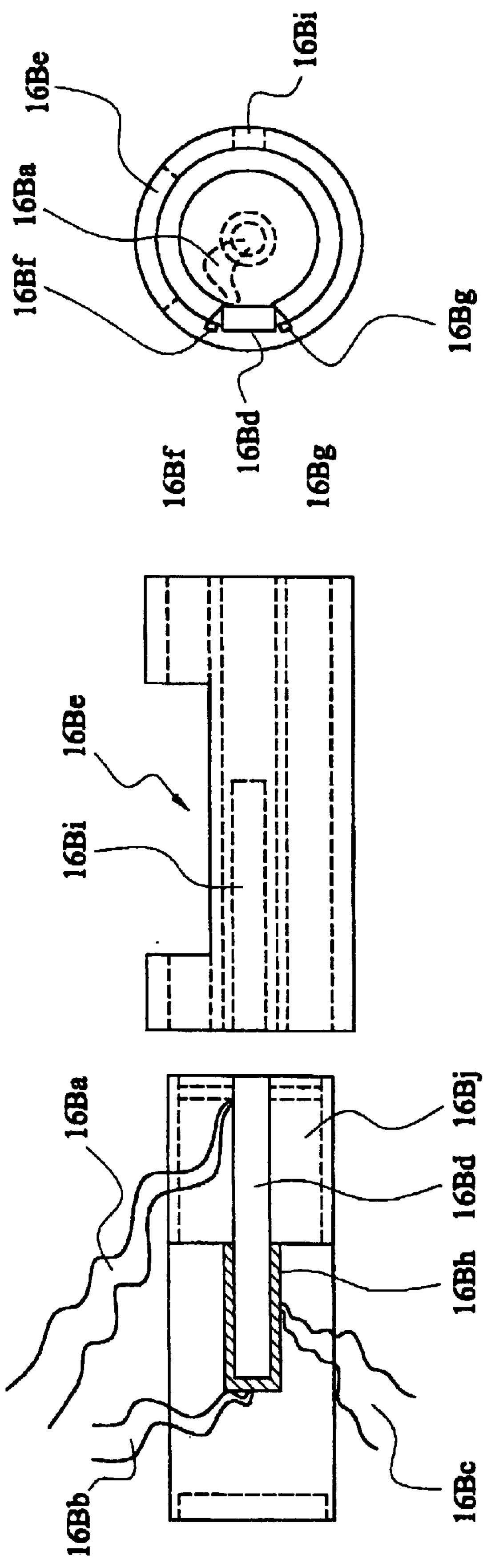

In FIG. 16B, the photodiode ribbon cable has been omitted from the drawings for clarity. The exploded view shows how the restraining sleeve slides over the heat shroud and Peltier exhaust. In this stage, the laser module and thermistor lead-outs (16Ba and 16Bb) which are thermally passive are fed down a first conduit (16Bf) of the restraining sleeve, whilst the thermally active lead-outs of the inner Peltier (16Bc) are fed down a second conduit (16Bg). The sleeve runs down the length of the exhaust strip (16Bd) firmly restraining the strip on the inner Peltier assembly at one end and the exhaust plate at the other. The sleeve cam then be slid over the construction with the lead-outs being fed down the appropriate conduits as the sleeve progresses. The aperture (16Be) expose a significant area of the copper heat shroud to enable the closing stages of construction to proceed.

Figure 17A:
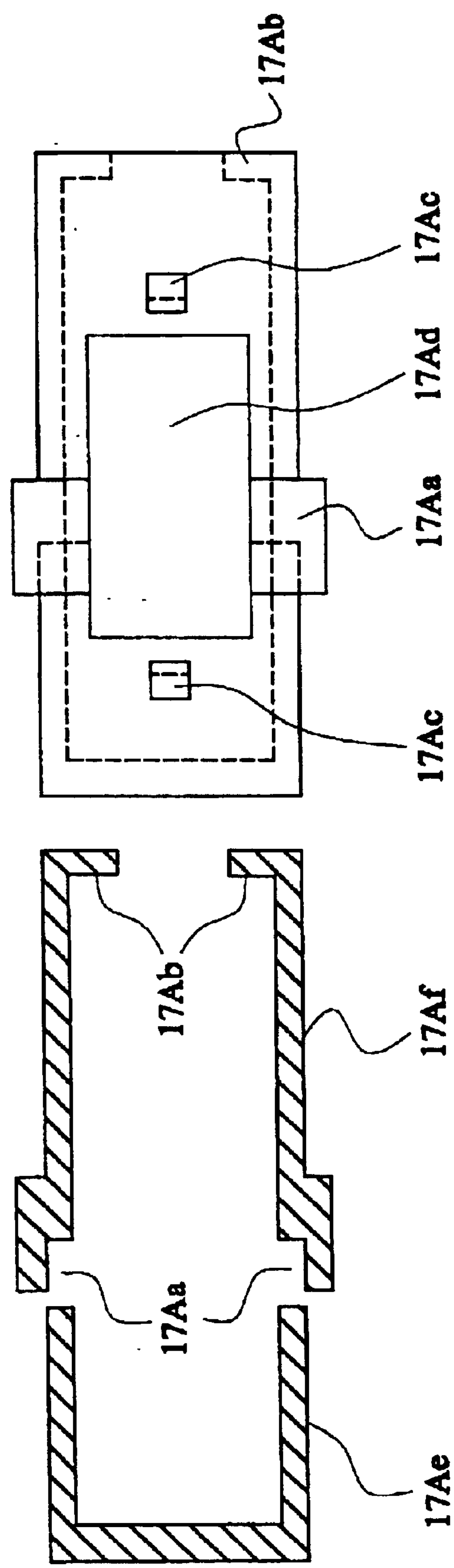
Figure 17B:
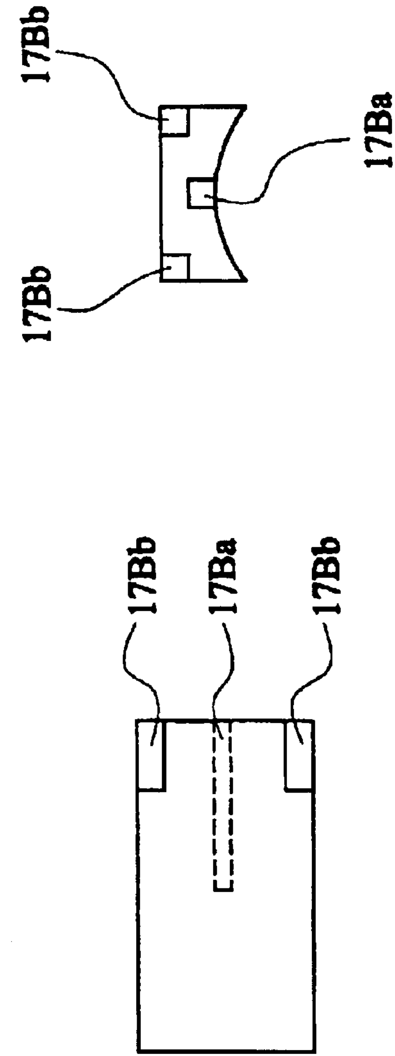

In FIGS. 17A and 17B, the outer casing is shown in sparing detail in side elevation and cross-section. It is constructed in two parts from an insulating engineering material. The upper part (17Ae) provides a thermal void (heated by the end plate of the optical assembly that is in thermal contact with the copper,shroud) in which the control electronics reside. The main part of the outer casing (17Af) 'snap fits' to the upper half at the joint (17Aa). The shoulder (17Ab) retains the exhaust plate. An aperture (17Ad) is provided to allow full access for an outer Peltier assembly. Two hooks are provided (17Ac) which enable the spring clip of the CPU heat sink and fan assembly to be employed to force it on to the rest of the assembly. This has been depicted as using the clip longitudinally. This tends to put stress on the joint (17Aa) which is undesirable. An alternative strategy is to mount the spring clip hooks laterally with both hooks on either the upper part (17Ae) or the main part (17Af) of the outer casing. A means for mounting the outer casing to a base plate or other component may be provided if desired.

Figure 18:
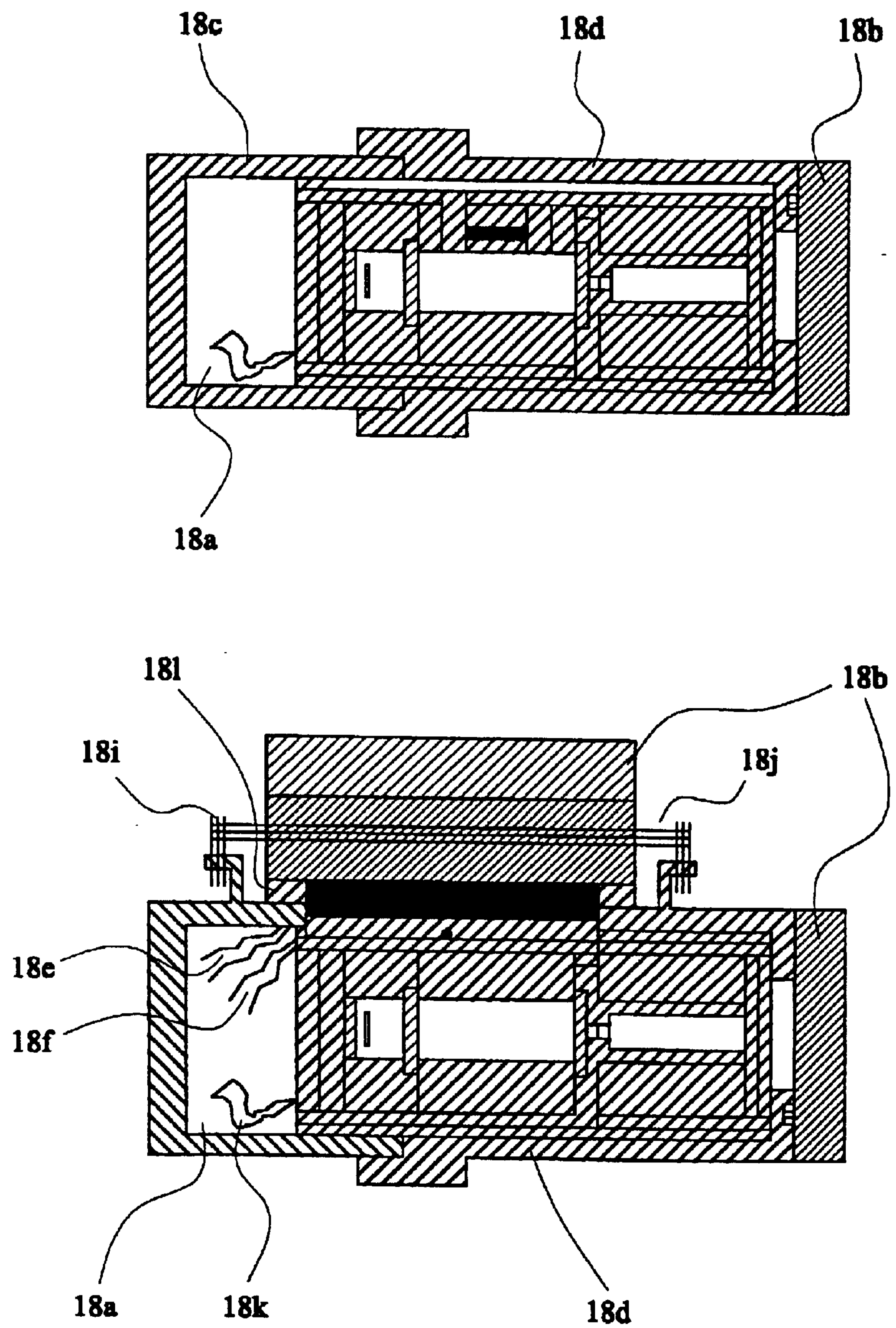

The outer Peltier mount of the outer Peltier assembly illustrated in FIG. 17B is similar to (although much larger than) that of the inner Peltier mount. It provides a large area of thermal contact with the copper heat shroud. A conduit mounts the thermistor (17Ba) and channels (17Bb) provide a means to effect the Peltier lead-out. The restraining sleeve and outer casing provide the coarse alignment of outer Peltier and outer Peltier mount. The fully assembled device is illustrated in FIG. 18 in two side elevation views (at 90° to each other). In the leftmost illustration, the void for the electronics is clearly visible (18*a*) which is provided by the upper part of the outer casing (18*c*). The main body of the outer casing (18*d*) provides a mount for a cooling fan (18*b*) for the inner Peltier exhaust plate. However it may be possible (and expedient) to include a second pair of hooks to enable the use of a second CPU heat sink/cooling fan spring clip system.

In the rightmost illustration, the lead outs from the outer Peltier and thermistor pairing (18*e* and 18*f*) and the photodiode ribbon cable (18*k*) are shown. The lead-outs from the laser module and the inner Peltier assembly have been omitted for clarity. The outer Peltier mount (18*h*) can be seen with the thermistor in place upon which is positioned the outer Peltier (18*g*). The CPU heat sink (18*j*) and fan assembly (18*b*) are retained on the Peltier (18*g*) by the spring clip (18*i*). Insulating foam (18*l*) has been placed around the perimeter of the outer Peltier (18*g*) where it is exposed to the external environment.

The key appropriate to FIG. 18 is as follows:

Good insulator & mechanical properties

Thermal drive (good thermal conductor)

Thermal exhaust (good themal conductor)

High performance insulator & Mechanical properties

High performance insulator

Secondary components (e.g., Fan)

CPU cooling fan retaining spring

Peltier

What is claimed is:

1. A device for housing a planar optical component for use in sensing, said device comprising:

an optical assembly adapted to mount the planar optical component so as to define a longitudinal path through the device in which the planar optical component is effectively exposed in free space and including guiding means for correlating along said longitudinal path the position of said planar optical component and of a source of electromagnetic radiation, whereby to expose said planar optical component to said electromagnetic radiation along said longitudinal path whilst substantially eliminating stray electromagnetic radiation, wherein the optical assembly comprises a cavity which permits access to a face of the planar optical component or to a face of a base with which the planar optical component is in intimate thermal contact whereby to enable an inner temperature controller to be positioned in thermal contact with the planar optical component for controlling the temperature of the planar optical component, wherein the inner temperature controller is an inner Peltier assembly capable of adding heat to or dissipating heat from the planar optical component, said inner Peltier assembly comprising an inner Peltier mounted on an inner Peltier mount, and a Peltier exhaust assembly which permits thermal transfer from an exhaust side of the inner Peltier to the environment.

2. A device as claimed in claim 1 wherein the Peltier mount has a concave underside to optimise thermal contact with the planar optical component or with a base with which the planar optical component is in intimate thermal contact.

3. A device as claimed in claim 1 wherein the planar optical component is a sensor.

4. A device as claimed in claim 3 wherein the sensor is mounted on a sensor base and is in intimate thermal contact therewith.

5. A device as claimed in claim 1 wherein the optical assembly and inner temperature controller are contained within a conducting sleeve.

6. A device as claimed in claim 5 wherein the conducting sleeve comprises a copper heat shroud.

7. A device as claimed in claim 6 wherein the copper heat shroud is provided with an opening which is suitably disposed to coincide with the cavity in the optical assembly thereby allowing the inner Peltier assembly to be inserted in the optical assembly after the optical assembly has been inserted in the conducting sleeve.

8. A device as claimed in claim 6 wherein the heat shroud comprises an integral laser module holder for inserting a laser module.

9. A device as claimed in claim 1 wherein the Peltier exhaust assembly comprises: an exhaust plate positioned to allow thermal exchange with the environment.

10. A device as claimed in claim 1 wherein the Peltier exhaust assembly comprises: means for thermally contacting the inner Peltier assembly with the exhaust plate.

11. A device as claimed in claim 10 wherein the means for thermally contacting the inner Peltier assembly with the exhaust plate is a thermally conducting exhaust strip.

12. A device as claimed in claim 1 wherein the Peltier exhaust assembly comprises: an exhaust guide capable of fitting over the insulating collar of a laser module.

13. A device as claimed in claim 12 wherein the exhaust guide defines a slot into which the thermally conducting exhaust strip may be inserted.

14. A device as claimed in claim 1 further comprising: an outer temperature controller which permits coarse temperature control of one or more of the group selected from the conducting sleeve, laser module, laser-module holder, the exterior parts of the optical assembly and the electronics.

15. A device as claimed in claim 14 wherein the outer temperature controller takes the form of an outer Peltier assembly.

16. A device as claimed in claim 15 comprising: means for urging the Peltier exhaust assembly onto the inner Peltier assembly.

17. A device as claimed in claim 16 wherein the means for urging is a restraining sleeve added outwardly of the heat shroud to force the Peltier exhaust assembly onto the inner Peltier assembly at a first end and the exhaust plate at the other.

18. A device as claimed in claim 17 wherein the outer Peltier assembly is provided externally of the restraining sleeve, said restraining sleeve provided with an aperture to enable exposure of an effective area of the conducting sleeve to achieve thermal contact with the outer Peltier assembly.

19. A device as claimed in claim 1 which is capable of sequential construction from a plurality of discrete assemblies, said assemblies being:

an optical assembly contained within a conducting sleeve;

an inner Peltier assembly comprising an inner Peltier; and a Peltier exhaust assembly, wherein: (1) the inner Peltier assembly is housed within the cavity of the optical assembly so as to achieve intimate thermal contact with the planar optical component and (2) the Peltier exhaust assembly permits thermal transfer from the exhaust side of the inner Peltier to the environment and is thermally isolated from the conducting sleeve.

20. A device as claimed in claim 19 further comprising a discrete outer Peltier assembly in thermal contact with the conducting sleeve.

21. A device as claimed in claim 1 wherein the planar optical component has a plurality of waveguides.

22. A process for constructing a device for housing a planar optical component for use in sensing, said device comprising an optical assembly adapted to mount the planar optical component so as to define a longitudinal path through the device in which the planar optical component is effectively exposed in free space and including guiding means for correlating along said longitudinal path the position of said planar optical component and of a source of electromagnetic radiation, whereby to expose said planar optical component to said electromagnetic radiation along said longitudinal path whilst substantially eliminating stray electromagnetic radiation, wherein the optical assembly comprises a cavity which permits access to a face of the planar optical component or to a face of a base with which the planar optical component is in intimate thermal contact whereby to enable an inner temperature controller to be positioned in thermal contact with the planar optical component for controlling the temperature of the planar optical component, the process comprising the steps of:

inserting an optical assembly in a conducting sleeve comprising an integral laser module housing;

inserting a laser module into the laser module housing;

housing an inner Peltier assembly in the cavity of the optical assembly so as to achieve thermal contact with the planar optical component; and positioning a Peltier exhaust assembly in thermal isolation from the conducting sleeve so as to permit thermal transfer from the exhaust side of the inner Peltier to the environment.

23. A process as claimed in claim 22 comprising the additional steps of:

constructing an outer restraining sleeve;

constructing an outer casing; and positioning an outer Peltier assembly on the outer casing or restraining sleeve whereby to achieve thermal contact with the conducting sleeve.

24. A device for housing a planar optical component for use in sensing, said device comprising:

an optical assembly adapted to mount the planar optical component so as to define a longitudinal path through the device in which the planar optical component is effectively exposed in free space and including guiding means for correlating along said longitudinal path the position of said planar optical component and of a source of electromagnetic radiation, whereby to expose said planar optical component to said electromagnetic radiation along said longitudinal path whilst substantially eliminating stray electromagnetic radiation, wherein the optical assembly comprises a cavity which permits access to a face of the planar optical component or to a face of a base with which the planar optical component is in intimate thermal contact whereby to enable an inner temperature controller to be positioned in thermal contact with the planar optical component for controlling the temperature of the planar optical component, wherein the optical assembly and inner temperature controller are contained within a conducting sleeve comprising a copper heat shroud, and wherein the copper heat shroud is provided with an opening which is suitably disposed to coincide with the cavity in the optical assembly thereby allowing the inner temperature controller to be inserted in the optical assembly after the optical assembly has been inserted in the conducting sleeve.

25. A device as claimed in claim 7 wherein the inner temperature controller is an inner Peltier assembly capable of adding heat to or dissipating heat from the planar optical component.

26. A device as claimed in claim 25 wherein the inner Peltier assembly comprises: an inner Peltier mounted on an inner Peltier mount.

27. A device as claimed in claim 26, wherein the Peltier mount has a concave underside to optimise thermal contact with the planar optical component or with a base with which the planar optical component is in intimate thermal contact.

28. A device as claimed in claim 24, wherein the heat shroud comprises an integral laser module holder for inserting a laser module.

29. A device as claimed in claim 26, further comprising a Peltier exhaust assembly which permits thermal transfer from an exhaust side of the inner Peltier to the environment.

30. A device as claimed in claim 29, wherein the Peltier exhaust assembly comprises: an exhaust plate positioned to allow thermal exchange with the environment.

31. A device as claimed in claim 29, wherein the Peltier exhaust assembly comprises: means for thermally contacting the inner Peltier assembly with the exhaust plate.

32. A device as claimed in claim 31, wherein the means for thermally contacting the inner Peltier assembly with the exhaust plate is a thermally conducting exhaust strip.

33. A device as claimed in claim 29, wherein the Peltier exhaust assembly comprises: an exhaust guide capable of fitting over the insulating collar of a laser module.

34. A device as claimed in claim 33, wherein the exhaust guide defines a slot into which the thermally conducting exhaust strip may be inserted.

35. A device for housing a planar optical component for use in sensing, said device comprising: an optical assembly adapted to mount the planar optical component so as to define a longitudinal path through the device in which the planar optical component is effectively exposed in free space and including guiding means for correlating along said longitudinal path the position of said planar optical component and of a source of electromagnetic radiation, whereby to expose said planar optical component to said electromagnetic radiation along said longitudinal path whilst substantially eliminating stray electromagnetic radiation, wherein the optical assembly comprises a cavity which permits access to a face of the planar optical component or to a face of a base with which the planar optical component is in intimate thermal contact whereby to enable an inner temperature controller to be positioned in thermal contact with the planar optical component for controlling the temperature of the planar optical component; an outer temperature controller which permits coarse temperature control of one or more of the group selected from the conducting sleeve, laser module, laser-module holder, the exterior parts of the optical assembly and the electronics, wherein the outer temperature controller takes the form of an outer Peltier assembly; and means for urging the Peltier exhaust assembly onto the inner Peltier assembly wherein the means for urging is a restraining sleeve added outwardly of the heat shroud to force the Peltier exhaust assembly onto the inner Peltier assembly at a first end and the exhaust plate at the other.

36. A device as claimed in claim 35, wherein the outer Peltier assembly is provided externally of the restraining sleeve, said restraining sleeve provided with an aperture to enable exposure of an effective area of the conducting sleeve to achieve thermal contact with the outer Peltier assembly.

37. A device for housing a planar optical component for use in sensing, said device comprising: an optical assembly adapted to mount the planar optical component so as to define a longitudinal path through the device in which the planar optical component is effectively exposed in free space and including guiding means for correlating along said longitudinal path the position of said planar optical component and of a source of electromagnetic radiation, whereby to expose said planar optical component to said electromagnetic radiation along said longitudinal path whilst substantially eliminating stray electromagnetic radiation, wherein the optical assembly comprises a cavity which permits access to a face of the planar optical component or to a face of a base with which the planar optical component is in intimate thermal contact whereby to enable an inner temperature controller to be positioned in thermal contact with the planar optical component for controlling the temperature of the planar optical component, wherein said device is capable of sequential construction from a plurality of discrete assemblies, said assemblies being:

an optical assembly contained within a conducting sleeve;

an inner Peltier assembly comprising an inner Peltier; and a Peltier exhaust assembly, wherein: (1) the inner Peltier assembly is housed within the cavity of the optical assembly so as to achieve intimate thermal contact with the planar optical component and (2) the Peltier exhaust assembly permits thermal transfer from the exhaust side of the inner Peltier to the environment and is thermally isolated from the conducting sleeve.

* * * * *

UNITED STATES PATENT AND TRADEMARK OFFICE

CERTIFICATE OF CORRECTION

PATENT NO. : 6,764,226 B1
DATED : July 20, 2004
INVENTOR(S) : Neville John Freeman It is certified that error appears in the above-identified patent and that said Letters Patent is hereby corrected as shown below:

Title page,
Item [73], Assignee, please delete "Fairfield" and insert therefor -- Farfield --.

Signed and Sealed this

Thirtieth Day of November, 2004

JON W. DUDAS
*Director of the United States Patent and Trademark Office*